United States Patent
Pierrard et al.

(10) Patent No.: US 7,361,507 B1
(45) Date of Patent: Apr. 22, 2008

(54) METHOD FOR MODULATING NITRILASE SELECTIVITY, NITRILASES OBTAINED BY SAID METHOD AND USE THEREOF

(75) Inventors: Jérôme Pierrard, Lyons (FR); Olivier Favre-Bulle, Lyons (FR); Catherine Jourdat, Sainte-Foy-lès-Lyon (FR)

(73) Assignee: Aventis Animal Nutrition S.A., Antony (FR)

( * ) Notice: Subject to any disclaimer, the term of this patent is extended or adjusted under 35 U.S.C. 154(b) by 101 days.

(21) Appl. No.: 10/129,560

(22) PCT Filed: Oct. 30, 2000

(86) PCT No.: PCT/FR00/03028

§ 371 (c)(1),
(2), (4) Date: Nov. 22, 2002

(87) PCT Pub. No.: WO01/34786

PCT Pub. Date: May 17, 2001

(30) Foreign Application Priority Data

Nov. 8, 1999 (FR) .................................. 99 14249

(51) Int. Cl.
*C12N 15/00* (2006.01)
*C12Q 1/34* (2006.01)
*C12N 9/78* (2006.01)
*C12P 21/06* (2006.01)
*G01N 33/00* (2006.01)
*C07K 14/00* (2006.01)
*C07H 21/04* (2006.01)

(52) U.S. Cl. ...................... 435/440; 435/227; 435/18; 435/69.1; 436/94; 530/350; 536/23.2

(58) Field of Classification Search ................ 435/227, 435/18, 69.1, 440; 436/94; 530/350; 536/23.2
See application file for complete search history.

(56) References Cited

OTHER PUBLICATIONS

Witkowski et al., Biochemistry 38:11643-11650, 1999.*
Seffernick et al., J. Bacteriol. 183(8):2405-2410, 2001.*
Brenner, Current Opinions in Structural Biology 12:775-782, 2002.*
Kobayashi, M et al., "Nitrilase in Biosynthesis of the Plant Hormone Indole-3-Acetic Acid from Indole-3-Acetonitrile: Cloning of the Alcaligenes Gene and site-directed Mutagenesis of Cysteine Residues", Proceedings of the National Academy of Sciences of USA, vol. 90, Jan. 1, 1993, p. 247-251.
Komeda, H et al., "Transcriptional Regulation of the *Rhodococcus rhodochrous* J1 Nita Gene Encoding a Nitrilase", Proceedings of the National Academy of Sciences of USA, vol. 93, No. 20, Oct. 1, 1996, p. 10572-10577.
Kobayashi, M et al., "Nitrilase from *Rhodococcus rhodochrous* J1. Sequencing and overexpression of the Gene and Identification of an Essential Cysteine Residue", Journal of Biological Chemistry, vol. 267, No. 29, Oct. 15, 1992, p. 20746-20751.
Watanabe, A et al., "Cloning and expression of a gene encoding cyanidase from Pseudomonas stutzeri AK61.", Applied Microbiology and Biotechnology, vol. 50, No. 1, Jul. 1998, p. 93-97.
Watanabe, A et al., "Investigation of the potential active site of a cyanide dihydratase using site-directed mutagenesis", Biochemica et Biophysica Acta, vol. 1382, No. 1, Jan. 15, 1998, p. 1-4.
Levy-Schil, Sophie et al., "Aliphatic nitrilase from a soil-isolated *Comamonas testosteroni* sp.: Gene cloning and overexpression, purification and primary structure", Gene, vol. 161, No. 1, 1995, p. 15-20.
Novo, Carlos et al., "Pseudomonas aeruginosa aliphatic amidase is related to the nitrilase/cyanide hydratase enzyme gamily and Cys-166 is predicted to be the active site nucleophile of the catalytic mechanism", Febs Letters, vol. 367, No. 3, 1995, p. 275-279.
Bork, Peer et al., "A new family carbon-nitrogen hydrolases.", Protein Science, vol. 3, No. 8, 1994, p. 1344-1346.
International Search Report Dated Feb. 9, 2001.

* cited by examiner

*Primary Examiner*—Delia M. Ramirez
(74) *Attorney, Agent, or Firm*—Finnegan, Henderson, Farabow, Garrett & Dunner LLP

(57) ABSTRACT

The invention concerns a modified nitrilase with modulated selectivity, characterized in that it comprises in position 162 an amino acid residue different from the original amino acid residue.

3 Claims, 6 Drawing Sheets

```
                  1                                                          50
p_Athalia1        ----------   ---------- -MSSTKDMS TVQNATPENG VAPST.TVRV TIVQSSTVYN
p_Athalia2        ----------   ---------- ------MS  TSEN.TPENG VASST.IVRA TIVQASTVYN
p_Athalia3        ----------   ---------- -MSSTEEMS SVRNTTQVIG VDPSS.TVRV TIVQSSTVYN
p_Tobacco1        ----------   -------MAL VPTPAVNEGP LFAEVDM..G DNSSTPTVRA TVVQASTIFY
p_Tobacco2        ----------   -------MAL VPTPVVNEGP MPAEVDM..G DNSSTPTVRA TVVQASTIFY
p_Osativa         ----------   ------MAM  VPSGSGGGPP VIAEVEMNGG ATSGAATVRA TVVQASTVFY
p_Athalia4        MSMQQETSHM   TAAPQTNGHQ IFPEIDMSAG DSSS...IVRA TVVQASTVFY
b_RrhodocJ1       ----------   ---------- ---------- ---------- MVEYTNTFKV AAVQAQPVWF
b_RrhodocPA3      ----------   ---------- ---------- ---------- MVEYTNTFKV AAVQAQPVWF
b_Gterrae         ----------   ---------- ---------- ---------M TTDYSGTFKA AVTQAEPVWF
b_RrhodocK22      ----------   ---------- ---------- ----MSSNP  ELKYTGKVKV ATVQAEPVIL
b_Kozaenae        ----------   ---------- ---------- ---------- ---MDTTFKA AAVQAEPVWM
b_CtestosNI1      ----------   ---------- ---------- ---------- -MKNYPTVKV AAVQAAPVFM
b_Afaecalis       ----------   ---------- ---------- ---------- -MQTRKIVRA AAVQAASPNY
Consensus         ----------   --------MA- VP-PSTNEM- TFAEV-M-NG --SSTPTVRA --VQASTVFY
                                                                                19

51                                                         100
p_Athalia1        DTPATIDKAE   KYIVEAASKG AELVLFPEGF IGGYPRGFRF G....LAVGV
p_Athalia2        DTPATLEKAN   KFIVEAASKG SELVVFPEAF IGGYPRGFRF G....LGVGV
p_Athalia3        DTPATLDKAE   KFIVEAASKG AKLVLFPEAF IGGYPRGFRF G....LAVGV
p_Tobacco1        DTPATLVKAE   RLLAEAASYG AQLVVFPEAF IGGYPRGSTF G....VSIGN
p_Tobacco2        DTPATLDKAE   RLLAEAASYG AQLVVFPEAF IGGYPRGSTF G....VSIGN
p_Osativa         DTPATLDKAE   RLIEEAAGYG SQLVVFPEAF VGGYPRGSTF GFGANISIGN
p_Athalia4        DTPATLDKAE   RLLSEAAENG SQLVVFPEAF IGGYPRGSTF ....ELAIGS
b_RrhodocJ1       DAAKTVDKTV   SIIAEAARNG CELVAFPEVE IPGYP...... ...YHIWVDS
b_RhodocPA3       DAAKTVDKTV   SIIAEAARNG CELVAFPEVF IPGYP...... ...YHIWVDS
b_Gterrae         DLSATVDKTI   ALVEEASRAG ADLIAFPETW IPGYP...... ...WFLWLDS
b_RrhodocK22      DADATIDKAI   GFIEEAAKNG AEFLAFPEVW IPGYP...... ...YWAWIGD
b_Kozaenae        DAAATADKTV   TIJVAKAAAG AQLVAFPELW IPGYP...... ...GFM.LTH
b_CtestosNI1      NLEATVDKTC   KIAEAASMG  AKVIGFPEAF IPGYP...... ...YWIMTSN
b_Afaecalis       DLATGVDKTI   ELARQARDEG CDLIVEGETH LPGYP...... ...FHVWLGA
Consensus         DTPATLDKAE   -LIAEAASNG A-LVVFPEAF I-GYPRGSTF G---YHLW-G-
```

Figure 1A

```
                   101                                                      150
p_Athalia1    HNEEGRDEFR KYHASAIHVP GPEVARLADV ARKNHVYLVM GAIEKEGYTL
p_Athalia2    HNEEGRDEFR KYHASAIKVP GPEVEKLAEL AGKNNVYLVM GAIEKDGYTL
p_Athalia3    HNEEGRDEFR NYHASAIKVP GPEVERLAEL AGKQNVHLVM GAIEKDGYTL
p_Tobacco1    RTAKGKEEFR KYHASAIDVP GPEVDRLAAM AGKYKVYLVM GVIERDGYTL
p_Tobacco2    RTAKGKEEFR KYHASAIDVP GPEVDRLAAM AGKYKVYLVM GVIERDGYTL
p_Osativa     PKDKGKEEFR KYHAAAIEVP GPEVTRLAAM AGKYKVFLVM GVIEREGYTL
p_Athalia4    RTAKGRDDFR KYHASAIDVP GPEVERIALM AKKYKVYLVM GVIEREGYTL
b_RrhodocJ1   PLAGMAKEAV RYHENSLTMD SPHVQRLLDA ARDRNIAVVV GISERDGGSL
b_RrhodocPA3  PLAGMAKEAV RYHENSLTMD SPHVQRLLDA ARDHNIAVVV GISERDGGSL
b_Gterrae     .VAWQSQYFI RYPQNSLDLD CSEFAAIREA ARRNDIAITM GFSERGHGSL
b_RrhodocK22  VKWAVSDFIP KYHENSLTLG RYPQNSLDLD ARQNNIALVM GYSEKDGASR
b_Kozaenae    NQTETLPFII KYRKQAIAAD DDRMRPLQLA GPEIEKIRCA GYSERAGRTL
b_CtestosN1   MDFTGMMWAV LF.KNAIEIP SKEVQQISDA AQEHNIALSF GYSERAGRTL
b_Afaecalis   P.AWSLKYSA RYYANSLSLD SAEFQRLAQA AKKNGVYVCV SVSEKDNASL
  Consensus   P-A-GRDEFR KYHA-AIDVP GPEV-RLADA ARKNVYLVM  GV-ERDGYTL
                62                                                       110

151                                                     200
p_Athalia1    YCTVLFFSPQ GQFLGKHRKL MPTSLERCIW GQGDGSTIPV YDTPIGKLGA
p_Athalia2    YCTALFFSPQ GQFLGKHRKL MPTSLERCIW GQGDGSTIPV YDTPIGKLGA
p_Athalia3    YCTALFFSPQ GQFLGKHRKV MPTSLERCIW CQGDGSTIPV YDTPIGKIGA
p_Tobacco1    YCTVLFFDSQ GHFLGKHRKI MPTALERIIW GFGDGSTIPV YDTPLGKIGA
p_Tobacco2    YCTVLFFDSQ GHYLGKHRKI METALERIIW GFGDGSTIPV YDTPLGKIGA
p_Osativa     YCSVLFFDPL GRYLGKHRKL METALERGIW GFGDGSTIPV YDTPLGKIGA
p_Athalia4    YCTVLFFDSQ GLFLGKHRKL METALERGIW GFGDGSTIPV FDTPIGKIGA
b_RrhodocJ1   YMTQLVIDAD GQLVARRRKL KPTHVERSVY CEGNGSDISV YDMPFARLGA
b_RrhodocPA3  YMTQLIIDAD GQLVARRRKL KPTHVERSVY GEGNGSDISV YDMPFARLGA
b_Gterrae     YMGQAVIERD GVVVRTRRKL KPTHVERTLF GEGDGSDLVV DQTSLGRVGS
b_RrhodocK22  YLSQVFIDQN GDIVANRRKL KPTHVERTIY GEGNGTDFLT HDFGFGRVGG
b_Kozaenae    YMSQMLIDAD GITKIRRRKL KPTRFERELF GEGDGSDLQV AQTSVGRVGA
b_CtestosN1   YLTQLMFDPN GNLIGKHRKF KPTSSERAVW GDGDGSMAFV FKTEYGNLGG
b_Afaecalis   YLGQCLIDDK GQMLWSRRKL KPTHVERTVF GEGYARDLIV BDTELGRVGA
  Consensus   YCTQLFFDPQ GQFLGKHRKL -PTHLERCIW GEGDGSTIPV YDTPLGK-GA
                111                                                      160
```

Figure 1B

```
201                                                                           250
p_Athalia1    AICWENRMPL YRTALYAKGI ELYCA..PTA DGSKEWQSSM L.........
p_Athalia2    AICWENRMPL YRTALYAKGI ELYCA..PTA DGSKEWQSSM L.........
p_Athalia3    AICWENRMPL YRTALYAKGI EIYCA..PTA DYSLEWQASM I.........
p_Tobacco1    AICWENRMPL LRTAMYAKGI EIYCA..PTA DSRDVWQASM T.........
p_Tobacco2    AICWENRMPL LRTAMYAKGI EIYCA..PTA DSRDVWQASM T.........
p_Osativa     LICWENKMPL LRTALYGKGI EIYCA..PTA DSRQVWQASM T.........
p_Athalia4    AICWENRMPS LRTAMYAKGI EIYCA..PTA DSRETWLASM T.........
b_RrhodocJ1   LNCWEHFQTL TKYAMYSMHE QVHVASWPGM .........SLY QPEVPAFGVD
b_RrhodocPA3  LNCWEHFQTL TKYAMYSMHE QVHVASWPGM .........SLY QPEVPAFGVD
b_Gterrae     LCCWEHLQPL TKYAMYSQHE QIHIAAWPSF .........SIF PGAVYALGPE
b_RrhodocK22  LNCWEHFQPL SKYMMYSLNE QIHVASWPAM .........FAL TPDVHQLSVE
b_Kozaense    LNCAENLQSL NKFALAAEGE QIHISAMP.. .........F   TLGSPVLVGD
b_CtestosNi1  LQCWEHALPL NIAAMGSLNE QVHVASWPAF VPKGAVSSRV SSSVCASTNA
b_Afaecalis   LCCWEHLSPL SKYALYSQHE AIHIAAWPSF .........SLY SEQAHALSAK
Consensus     LICWENRMPL LRTAMYAKG- EI-CASWPTA DSR--WQSSM TPEVPALGVD
161                                                                           203

251                                                                                300
p_Athalia1    ........HIA IEGGCFVLSA CQFCQRKHFP DHPDYLFTDW YDDKEHDSIV
p_Athalia2    ........HIA IEGGCFVLSA CQFCLRKDFP DHPDYLFTDW YDDKEPDSIV
p_Athalia3    ........HIA VEGGCFVLSA HQFCKRREFP EHPDYLFNDI VDTKEHDPTV
p_Tobacco1    ........HIA LEGGCFVLSA NQFCRRKDYP PPPEYVFSGI EEDLTPDSIV
p_Tobacco2    ........HIA LEGGCFVLSA NQFCRRKDYP PPPEYVFSGT .EDLTPDSIV
p_Osativa     ........HIA LEGGCFVLSA NQFCRRKDYP PPPEYVFTGL GEEPSPDTVV
p_Athalia4    ........HIA LEGGCFVLSA NQFCRRKDYP SPPEYMFSGS EESLIPDSVV
b_RrhodocJ1   AQLTATRMYA LEGQTFVVCT TQVVTPEAHE .....FFC.D NDEQRKLIGR
b_RrhodocPA3  AQLTATRMYA LEGQTFVVCT TQVVTPEAHE .....FFC.E NEEQRKLIGR
b_Gterrae     VNTAASQQYA VEGQTYVLAP CAVIGDAGWE .....AFA.D TEEKRQLIHK
b_RrhodocK22  ANDTVTRSYA IEGGTFVLAS THVIGKATQD .....LFAGD DDAKRALLPL
b_Kozaense    SIGAINQVYA TQVVGPTGIA ........... .....AFEIE DRYNPNQY.L
b_CtestosNi1  MHQIISQFYA ISNQVYVIMS TNLVGQDMID .........MI.GK DEFSKNFLPL
b_Afaecalis   VNMAASQIYS VEGQCFTIAA SSVVTQETLD .........ML.EV GERNASLLKV
Consensus     ANL-A-QH-A LEGGCFVLSA TQFC-RKDYP PPPEYLF-GD DE-KRPDSIV
204                                                                               247
```

Figure 1C

```
            301                                                              350
p_Athalia1  SQGGSVIISP LGQVLAGP.N FESEGLVTAD IDLGDIARAK LYFDSVGYYS
p_Athalia2  SQGGSVIISP LGQVLAGP.N FESEGLITAD LDLGDVARAK LYFDSVGHYS
p_Athalia3  SGGGSVIISP LGKVLAGP.N YESEGLVTAD LDLGDIARAK LYEDVVGHYS
p_Tobacco1  CAGGSVIISP SCAVLAGP.N YVGEALISAD LDLGEIARAK FDFDVVGHYA
p_Tobacco2  CAGGSVIISP SGAVLAGP.N YEGEALISND LDLGEIARAK FDFDVVGHYA
p_Osativa   CPGGSVIISP SGEVLAGP.N YEGEALITAD LDLGEIVRAK FDFDVVGHYA
p_Athalia4  CAGGSSIISP LGIVLAGP.N YRGEALITAD LDLGDIARAK FDFDVVGHXA
b_RrhodocJ1 GGGFARIIGP DGRDLATPLA EDEEGILYAD IDLSAITLAK QAADPVGHYB
b_RrhodocPA3 GGGFARIIGP DGRDLATPLA EDEEGILYAD IDLSAITLAK QAADPVGHYS
b_Gterrae   GGGYARIYGP DGRSLAEPLA PNDEGILYAD IDLSAILAAK NPADPVGHYS
b_RrhodocK22 GQGWARIYGP DGKSLAEPLP EDAEGLLYAE LDLEQIILAK AAADPAGHYS
b_Kozaenae  GGGYARIYGP DMQLKSKSLS PTEEGIVYAE IDLSMLEAAK YSLDPTGHYS
b_CtestosN1 GSGNTAIISN TGEILAS.IP QDAEGIAVAE IDLNQIIYGK WLLDPAGHYS
b_Afaecalis GGGSSMIFAP DGRTLAPYLP HDAEGLIIAD LNMEEIAFAK AINDPVGHYS
Consensus   GGGGSVIISP DGRVLAGPLN Y-GEGLI-AD LDLG-IARAK FDFDPVGHYS
            248                                                              297

351                                                              400
p_Athalia1  RPDVLHLTVN EHPRKSVTFV TKVEKAEDDS NK---------
p_Athalia2  RPDVLHLTVN EHPKKPVTFI SKVEKAEDDS NK---------
p_Athalia3  KPDIENLTVN EHPKKPVTFM TKVEKAEDES NK---------
p_Tobacco1  RPEVLSLIVR DHAVSPVSF. TS.....TSS KAESSPK----
p_Tobacco2  RPEVLSLIVR DHAVSPVSF. TS.....TSS KAESSPK----
p_Osativa   RPEVLSLVVN DQPHLPVSF. TSAAEKTTAA KSDSTAKPY-
p_Athalia4  RPEVFSLNIR EHPRKAVSFK TSKVMEDESV ----------
b_RrhodocJ1 RPDVLSLNFN QRHTTPVNTA ISTI....HA THTLVPQSGA LDGVRELNGA
b_RrhodocPA3 RPDVLSLNFN QRRTTPVNTP LSTI....HA THTFVPQFGA LDGVRELNGA
b_Gterrae   RPDVLRLGFN KAPQPKVNI. LGT......EP SRTTSTQCRP TTIRRSWRFP
b_RrhodocK22 RPDVLSLKID TRNHTPVQYI TAD........ GRTSLNSNSR VENYRLHQLA
b_Kozaenae  RPDVFSVSIN RQRQPAVSEV I.DSNGDEDP RAACEPDEGD LVVISTAIG
b_CtestosN1 TPGFLSLTFD QSEHVPVKK. IGEQTNHFIS YEDLHEDKMD MLTIPPRRVA
b_Afaecalis KPEATRLVLD LGHREPMTRV HSKSVIQEEA PEPHVQSTAA PVAVSQTQDS
Consensus   RPDVLSLTVN EHP-KPVSFV TS-EKAE--S --TS-P--GA L-GVR---GA
            298                                                              347
```

Figure 1D

|              | 401              |          |            |            | 441 |
|--------------|------------------|----------|------------|------------|-----|
| p_Athalia1   | ~~~~~~~~~        | ~~~~~~~~ | ~~~~~~~~~~ | ~~~~~~~~~~ | ~   |
| p_Athalia2   | ~~~~~~~~~        | ~~~~~~~~ | ~~~~~~~~~~ | ~~~~~~~~~~ | ~   |
| p_Athalia3   | ~~~~~~~~~        | ~~~~~~~~ | ~~~~~~~~~~ | ~~~~~~~~~~ | ~   |
| p_Tobacco1   | ~~~~~~~~~        | ~~~~~~~~ | ~~~~~~~~~~ | ~~~~~~~~~~ | ~   |
| p_Tobacco2   | ~~~~~~~~~        | ~~~~~~~~ | ~~~~~~~~~~ | ~~~~~~~~~~ | ~   |
| p_Osativa    | ~~~~~~~~~        | ~~~~~~~~ | ~~~~~~~~~~ | ~~~~~~~~~~ | ~   |
| p_Athalia4   | ~~~~~~~~~        | ~~~~~~~~ | ~~~~~~~~~~ | ~~~~~~~~~~ | ~   |
| b_RrhodocJ1  | DEQRALPSTH       | SDETDRATAS | I~~~~~~~~ | ~~~~~~~~~~ | ~   |
| b_RrhodocPA3 | DEQRALPSTH       | SDETDRATAP | SDSGAPVAPP | KRHGV*~~~~ | ~   |
| b_Gterrae    | E*~~~~~~~        | ~~~~~~~~ | ~~~~~~~~~~ | ~~~~~~~~~~ | ~   |
| b_Rrhodock22 | DIEK......       | YENAEAAATLP | LDAPAPAPAP | EQKSGRAKAE | A   |
| b_Kozaenae   | VLPRYCGHS~       | ~~~~~~~~ | ~~~~~~~~~~ | ~~~~~~~~~~ | ~   |
| b_CtestosNI1 | TA~~~~~~~        | ~~~~~~~~ | ~~~~~~~~~~ | ~~~~~~~~~~ | ~   |
| b_Afaecalis  | DTLLVQEPS~       | ~~~~~~~~ | ~~~~~~~~~~ | ~~~~~~~~~~ | ~   |
| Consensus    | DEQRALPS-H       | SDETDRATAP | -D--AP---P | ---------- | -   |
|              | 348              |          |            |            |     |

Figure 1 E

METHOD FOR MODULATING NITRILASE SELECTIVITY, NITRILASES OBTAINED BY SAID METHOD AND USE THEREOF

This application is a national stage filing of International Application No. PCT/FR00/03028, filed Oct. 30, 2000. This application also claims the benefit of priority to FR 99/14, 249, filed on Nov. 8, 1999.

The present invention relates to novel nitrilases with enhanced selectivity, to the method for obtaining them and to the use of said nitrilases.

BRIEF DESCRIPTION OF THE DRAWINGS

FIGS. 1A-E show an alignment of the amino acid sequences of nitrilases from several species. The aligned amino acid sequences are p_Athalia1 (SEQ ID NO: 6), p_Athalia2 (SEQ ID NO: 7), p_Athalia3 (SEQ ID NO: 8), p_Tobacco1 (SEQ ID NO: 9), p_Tobacco2 (SEQ ID NO: 10), p_Osativa (SEQ ID NO: 11), p_Athalia4 (SEQ ID NO: 12), b_RhodocJ1 (SEQ ID NO: 13), b_RrhodocPA3 (SEQ ID NO: 14), b_Gterrae (SEQ ID NO: 15), b RrhodocK22 (SEQ ID NO: 16), b Kozaenae (SEQ ID NO: 17), b_CtestosNI1 (NitA; SEQ ID NO: 18), b_Afaecalis (SEQ ID NO: 19) and the consensus sequence (SEQ ID NO: 20). The numbers at the bottom of each sequence panel represent the amino acid position of the NitB (b_Afaecalis of *Alcaligenes faecalis*) reference sequence (SEQ ID NO: 19). The "**" indicator designates the amino acids of each sequence corresponding to positions 162 and 163 of NitB.

NITRILASES

Figure 2:
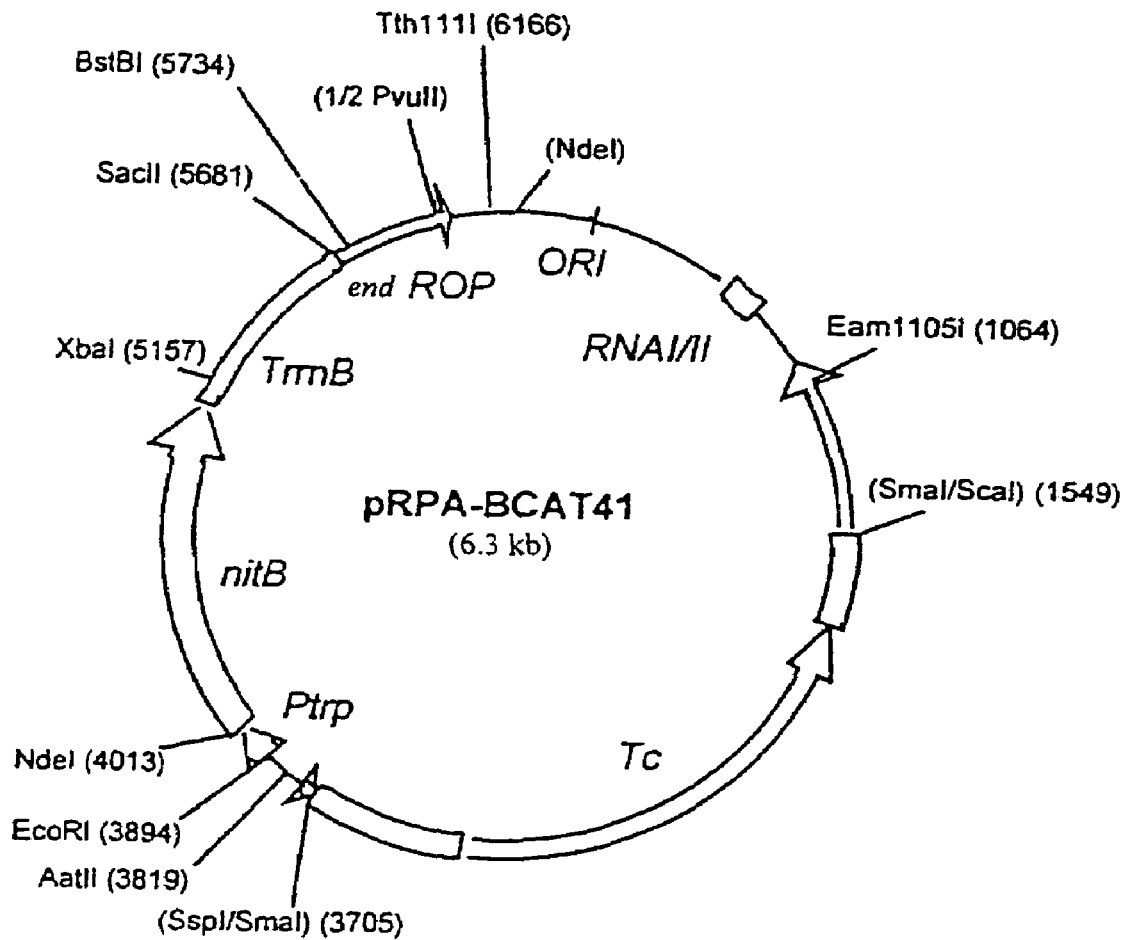
FIG. 2 shows a map of plasmid pRPA-BCAT41

Enzymes which catalyze the hydrolysis of nitrile groups to corresponding carboxylic acids and ammonium ions are nitrilases (Faber, Biotransformations in Organic Chemistry, Springer Verlag, Berlin Heidelberg, 1992, ISBN3-540-55762-8). However, this bioconversion of the nitrile groups to corresponding carboxylic acids, the final result of which consists of hydrolysis of the nitrile groups, may also be carried out in two steps, the first step consisting of the bioconversion of the nitrites to corresponding amides with a nitrile hydratase, the second step consisting in hydrolyzing the amides obtained to corresponding carboxylic acids with amidases.

Nitrilases were first discovered in plants (Thimann and Mahadevan, 1964, *Arch. Biochem. Biophys.* 105: 133-141) and then isolated in many representatives of soil microflora (Kobayashi and Shimizu, 1994, *FEMS Microbiology Letters* 120: 217-224): *Pseudomonas, Nocardia, Arthrobacter, Fusarium, Rhodoccocus, Klebsiella* and *Alcaligenes*. More recently, nitrilases have been characterized in thermophilic bacteria (Cramp et al., 1997, *Microbiology*, 143: 2313-2320). Nitrilases have varied substrate specificities but can be grouped into three groups depending on their specificity: nitrilases specific for aliphatic nitriles, those specific for aromatic nitrites or those specific for arylacetonitriles (Kobayashi et al., 1993, *Proc. Natl. Acad. Sci. USA* 90: 247-251; Kobayashi and Shimizu, 1994, mentioned above; Lévy-Schil et al., 1995, *Gene* 161: 15-20; Layh et al., 1998, J. Mol. Catal. B: Enzymatic 5: 467-474).

Nitrilases are of value in biocatalysis since many synthetic processes involve the hydrolysis of nitrile groups (Yamamoto et al., 1991, Appl. Environ. Microb. 57: 3028-3032; Faber, Biotransformations in Organic Chemistry, 2nd edn, Springer-Verlag, Berlin, 1995; Lévy-Schil et al., 1995, *Gene* 161: 15-20; Cowan et al., 1998, Extremophiles 2: 207-216): conversion of adiponitrile to cyanovalerate or adipate, synthesis of nicotinic acid, of p-aminobenzoic acid of tranexamic acid, enantioselective hydrolysis of mandelonitrile. In particular, the nitrilase of *Alcaligenes faecalis* ATCC8750 (called NitB in this application) and that of *Comamonas testosteroni* (called NitA in this application) may be used to attain the hydroxy analog of methionine (FR9411301, WO9609403, FR9613077).

Nitrilases have primary structures which align with variable degrees of identity, starting from approximately 30%. Aligning the sequences of several nitrilases reveals the conservation of several residues, including a cysteine residue at position 163 on the sequence of the NitB nitrilase. This residue is involved in the nitrilase reaction mechanism (Kobayashi et al., 1993, Proc. Natl. Acad. Sci. USA 90: 247-251).

For the present invention, the reference sequence is the NitB sequence, all the definitions and indications of particular amino acid positions being given relative to the NitB primary sequence. The attached FIG. 1 represents an alignment of 14 nitrilase sequences described in the state of the art, aligned relative to the NitB sequence as reference, comprising the sequences p_Athalia1 to 4 of *Arabidopsis thaliana* (SwissProt accession No.: P32961, P32962, P46010, P46011), p_Tobacco1 and 2 of *Nicotiana tabacum* (GeneBank accession No.: D63331, D83078), b_RhodocJ1 of *Rhodococcus rhodocrous* J1 (GeneBank accession No.: D11425), b_RrhodocPA3 of *Rhodococcus rhodocrous* PA34 (GeneBank accession No.: E09026), b_Gterrae of *Gordona terrae* (Genebank accession No. E12616), b_RrhodocK22 of *Rhodococcus rhodocrous* K22 (GeneBank accession No. D12583), b_Kozaenae of *Klebsiella ozaenae* (SwissProt accession No.: P100450), b_CtestosNI1 of *Comamonas testosteroni* NI1 or NitA (GeneBank accession No.: L32589), and b_Afaecalis of *Alcaligenes faecalis* JM3 or NitB (SwissProt accession No.: P20960). The numbering of the amino acids of the NitB sequence is given on this figure (numbering at the bottom), as is the consensus sequence with its numbering (numbering at the top). By convention in this application, the residues of the other nitrilases are numbered relative to this cysteine residue and to the sequence of the NitB nitrilase as reference sequence. Based on such an alignment, or on any nitrilase sequence of alignment, it is easy for those skilled in the art to identify, using the definition of the NitB amino acid given by its position and its nature, the position of the corresponding amino acid in another nitrilase sequence.

The Problem of Selectivity

Nitrilase selectivity is defined as the percentage of compounds not having a carboxylic function which are released by the nitrilase-catalyzed hydrolysis of a nitrile. It has been described relatively little, but is observed for a certain number of nitrilases and substrates. Thus, the hydrolysis of 2-methoxymandelonitrile to 2-methoxymandelic acid catalyzed by the nitrilase of *Pseudomonas fluorescens* DSM 7155 leads to the coproduction of 2-methoxy-mandelamide (Layh et al., 1998, mentioned above). Similarly, the hydrolysis of 2-hydroxy-4-methylthio-butyronitrile (HMTBN) catalyzed by the NitA nitrilase of *Comamonas testosteroni* NI1 (Lévy-Schil et al., 1995, mentioned above), described in the examples of this application, is accompanied by the coproduction of 2-hydroxy-4-methylthiobutyramide (HMTBM). In the case of a biocatalytic process using such an enzyme/substrate pair, the high selectivity of the nitrilase for its substrate leads to a coproduction of amide, which represents a loss of yield of the process. This loss of yield may have a considerable economic impact. In addition, this high selectivity leads to the presence of amide contaminating the reaction product. Purification of the carboxylic acid is then necessary and, here again, has an economic impact on the process. The high selectivity of a nitrilase for a given substrate is, consequently, an obstacle to the development of a biocatalytic process using this nitrilase and this substrate.

An increase in enzyme selectivity may also be sought if this increase is accompanied by an increase in the catalytic activity of the enzyme on its substrate. It is in particular the case in methods of decontamination in which rapid degradation of a toxic molecule with an enzyme with maximum specific activity is sought. In this case, the nature of the products derived from the reaction catalyzed by the enzyme has little importance relative to the rate of degradation of the substrate.

It is therefore particularly important to be able to modify nitrilase selectivity, both in terms of an enhancement of this selectivity and in terms of a decrease.

Enhancement of Enzymes

The directed evolution of an enzyme consists in adapting an enzyme to a particular function by repeatedly selecting variants which have enhanced properties (Arnold and Volkov, 1999, Current Opinion in Chemical Biology 3: 54-59; Kuchner and Arnold, 1997, Tibtech 15: 523-530). These variants may be created by several techniques of mutagenesis on the gene encoding the enzyme studied (Skandalis et al., 1997, Chemistry & Biology 4: 8889-898; Crameri et al., 1998, Nature 391: 288-291): chemical mutagenesis (Singer and Fraenkel-Conrat, 1969, Prog. Nucl. Acid Res. Mol. Biol. 9: 1-29), mutagenesis by error-prone PCR (Leung et al., 1989, Technique 1: 11-15), by combinatorial PCR (Crameri et al., 1998, mentioned above; Shao et al., 1998, Nucleic Acids Res. 26:681-683), by directed mutagenesis (Directed Mutagenesis: A Practical Approach, 1991, Edited by M. J. McPBERSON, IRL PRESS), etc.

In the context of a method for enhancing the activity of the NitB nitrilase on HMTBN (2-amino-4-methylthiobutyronitrile), the inventors have noted that a point substitution on NitB in the region of the active site at position 162, by replacing the cysteine residue with an asparagine residue, leads to modification of the selectivity of the nitrilase studied. On the other hand, they have noted that introducing a cysteine residue at position 162 on the sequence of the NitA nitrilase leads to reduction of its selectivity on another of its substrates, AMTBN, thus demonstrating that position 162 in the region of the active site of nitrilases is a key position involved in the selectivity of said nitrilases and that modification of the amino acid residue at this position, consisting in replacing the amino acid of origin with another amino acid, leads to a modulation of the selectivity of nitrilases.

The present invention therefore relates to a modified nitrilase with modulated selectivity, characterized in that it comprises, at position 162, an amino acid residue which is different from the amino acid residue of origin.

According to the invention, the term "modified nitrilase" is intended to mean a nitrilase which is modified relative to a nitrilase of origin, the modification consisting in replacing the amino acid residue of origin at position 162 with another amino acid.

According to the invention, the expression "modulation of the selectivity" is intended to mean a selectivity of the modified nitrilase which is different from the selectivity of the nitrilase of origin, in particular by at least 0.5% relative to the nitrilase of origin, advantageously by at least 1%.

Advantageously, residue 162 is replaced with an amino acid chosen from cysteine, alanine, valine, asparagine, glutamine, isoleucine and serine, it being understood that residue 162 of the nitrilase of origin is different from a cysteine, alanine, valine, asparagine, glutamine, isoleucine or serine, respectively.

Residue 162 is preferably replaced with a cysteine residue.

According to a particular embodiment of the invention, the modulation consists of an enhancement of the selectivity.

According to a second particular embodiment of the invention, the modulation consists of a decrease in the selectivity.

The unmodified nitrilase of origin is chosen from nitrilases of bacterial, yeast, fungal, plant or animal origin.

Among the nitrilases of bacterial origin, mention may be made, in particular, of the following nitrilases: b_RhodocJ1 of *Rhodococcus rhodocrous* J1 (GeneBank accession No.: D11425), b_RrhodocPA3 of *Rhodococcus rhodocrous* PA34 (GeneBank accession No.: E09026), b_Gterrae of *Gordona terrae* (GeneBank accession No.: E12616), b_RrhodocK22 of *Rhodococcus rhodocrous* K22 (GeneBank accession No.: D12583), b_Kozaenae of *Klebsiella ozaenae* (SwissProt: accession No.: P100450), b_CtestosNI1 of *Comamonas testosteroni* NI1 or NitA (GeneBank accession No.: L32589), and b_Afaecalis of *Alcaligenes faecalis* JM3 or NitB (SwissProt accession No.: P20960). Among the nitrilases of plant origin, mention may be made in particular of: p_Athalia1 to 4 of *Arabidopsis thaliana* (SwissProt accession No.: P32961, P32962, P46010, P46011), and p_Tobacco1 and 2 of *Nicotiana tabacum* (GeneBank accession No.: D63331, D83078).

Among the nitrilases of other origins, mention may be made in particular of: those of *Saccharomyces cerevisiae* (SwissProt accession No.: P40447 and P4044), of *Caenorhabditis elegans* (GeneBank accession No.: AF069986), of *Drosophila melanogaster* (GeneBank AF069989) of *Homo sapiens* (GeneBank accession No.: AF069987) and of *Mus musculus* (GeneBank accession No.: AF069988).

According to another embodiment of the invention, the nitrilase of origin is a nitrilase obtained by screening DNA libraries, in particular cDNA or genomic DNA from various sources, in particular DNA libraries obtained through random mutations and recombinations of nitrilases, by directed molecular evolution, or by screening a DNA library from soil or from other biotopes.

The present invention also relates to a nucleic acid sequence, in particular a DNA sequence, encoding a modified nitrilase above.

According to a first embodiment of the invention, the nucleic acid sequence according to the invention consists of the nucleic acid sequence of the nitrilase of origin, for which the codon of the residue of origin at position 162 has been replaced with a codon encoding a residue which is different from the residue of origin, in particular the codons encoding the residues alanine, valine, asparagine, glutamine, isoleucine or serine.

The codons of the sequence of origin may be modified by any means known to those skilled in the art for enhancing the enzymes defined previously, in particular by directed mutagenesis.

The present invention also relates to a chimeric gene or expression cassette, comprising, in the direction of transcription, a promoter regulatory sequence which is functional in a host organism, the nucleic acid sequence encoding a modified nitrilase according to the invention and a terminator regulatory sequence which is functional in the same host organism.

The host organism comprises any eukaryotic or prokaryotic organism, which may be differentiated or undifferentiated, in particular bacteria, yeasts, fungi, plant cells and plants.

They are in particular bacteria, for example *E. coli*, yeasts, in particular of the genera *Saccharomyces, Kluyveromyces* or *Pichia*, fungi, in particular of the genera *Aspergillus* or *Penicillium*, a baculovirus, or plant cells and plants.

According to the invention, the term "plant cell" is intended to mean any cell which is derived from a plant and which can constitute undifferentiated tissues such as calluses, differentiated tissues such as embryos, parts of plants, plants or seeds.

According to the invention, the term "plant" is intended to mean any differentiated multicellular organism capable of photosynthesis, in particular monocotyledons or dicotyledons, more particularly crop plants which may or may not be intended for animal or human food, such as maize, wheat, rapeseed, soybean, rice, sugar cane, beetroot, tobacco, cotton, etc.

The promoter and terminator regulatory elements are well known to those skilled in the art, depending on the host organisms.

As a regulatory sequence which is a promoter in bacteria, use may be made of any promoter regulatory sequence of a gene expressed naturally in bacteria, for example the promoter of the *E. coli* tryptophan operon (Denèfle et al., 1987, Gene 56: 61-70).

As a regulatory sequence which is a promoter in yeasts, use may be made of any promoter regulatory sequence of a gene expressed naturally in yeasts, for example the promoter of the *S. cerevisiae* Mfα1 gene or of the *Kluyveromyces lactis* lactase gene (van den Berg et al., 1990, Bio/Technology 8: 135-139).

As a regulatory sequence which is a promoter in fungi, use may be made of any promoter regulatory sequence of a gene expressed naturally in fungi, for example the promoter sequence of the *Penicillium chrysogenum* acid phosphatase gene (Graessle et al., 1997, Appl. Environ. Microbiol. 63:753-756) or the promoter sequence of the *Aspergillus nidulans* alcohol dehydrogenase I gene (Gwyne et al., 1989, Biochem. Soc. Trans. 17: 338-340).

As a regulatory sequence which is a promoter in plant cells and plants, use may be made of any promoter sequence of a gene expressed naturally in plants, in particular a promoter of bacterial, viral or plant origin, such as, for example, that of a gene of the ribulose-biscarboxylase/oxygenase (RuBisCO) small subunit, a histone promoter (EP 0 507 698), a rice actine promoter, or a promoter of a plant virus gene, such as, for example, that of the cauliflower mosaic virus (CAMV 19S or 35S), or a promoter inducible by pathogens, such as the tobacco PR-Ia, it being possible to use any suitable known promoter.

As a regulatory sequence which is a terminator in bacteria, use may be made of any terminator regulatory sequence of a gene expressed naturally in bacteria, for example the terminator regulatory sequence of the *E. coli* ribosomal RNA operon (Denèfle et al., 1987, Gene 56: 61-70).

As a regulatory sequence which is a terminator in yeasts, use may be made of any terminator regulatory sequence of a gene expressed naturally in yeasts, for example the terminator of *S. cerivisiae* phosphoglycerate kinase (PGK) or the terminator of *Kluyveromyces lactis* lactase (van den Berg et al., 1990, Bio/Technology 8: 135-139).

As a regulatory sequence which is a terminator in fungi, use may be made of any terminator regulatory sequence of a gene expressed naturally in fungi, for example the terminator regulatory sequence of the *Trichoderma reesei* pyruvate kinase gene (Schindler et al., 1993, Gene 130: 271-275).

As a regulatory sequence which is a terminator in plant cells or plants, use may be made of any terminator regulatory sequence of a gene expressed naturally in plants, for example the terminator of a gene of bacterial origin, such as for example the *Agrobacterium tumefaciens* nos terminator, of viral origin, such as for example the CaMV 35S terminator, or of plant origin, such as for example a histone terminator (EP 0 633 317).

The present invention also relates to a transformed host organism comprising a chimeric gene as defined above, in particular a host organism defined above into the genome of which the chimeric gene according to the invention has been stably integrated.

The present invention also relates to a method for producing modified nitrilases with reduced selectivity defined above, said method consisting in selectivity defined above, said method consisting in culturing the transformed host organism according to the invention and, where appropriate, in isolating the modified nitrilase, as a mixture or in a purified form.

The present invention also relates to the use of a modified nitrilase according to the invention, in a biocatalysis reaction in a method for synthesizing or degrading chemical compounds.

Finally, the present invention relates to a method for modulating nitrilase selectivity, said method comprising replacing residue 162, in a nitrilase of origin, with an amino acid residue which is different from the amino acid residue of origin. Advantageously, residue 162 is replaced by introducing, into the nucleic acid sequence encoding the unmodified nitrilase of origin, a codon encoding a residue at position 162 which is different from the codon encoding the residue of the nitrilase of origin.

Preferably, the nitrilase obtained using said modulation method is a nitrilase as defined above.

The examples below make it possible to illustrate the present invention, without seeking to limit the scope thereof.

MATERIALS AND METHODS

The nitrilase activity on 2-hydroxy-4-methyl-thiobutyronitrile is measured as follows:

A culture sample with a known optical density at 660 nm ($OD_{660}$) is taken and washed in 100 mM phosphate buffer, pH 7.0. Estimating the dry weight of the sample from the $OD_{660}$ (one $OD_{660}$ unit corresponds to a dry weight of 0.35 mg of dry cell/ml), approximately 1 mg of DC is taken up in 1 ml of 100 mM phosphate buffer, pH 7.0, and incubated in a closed 2-ml tube at 35° C. for 10 minutes. The kinetics are initiated by adding 17 µl of the solution of HMTBN at 78%, so as to achieve a concentration of 100 mM in the reaction mixture at the start of the assay. The reaction is incubated at 35° C. with stirring. Every 15 minutes, a 100 µl sample of the suspension is withdrawn and mixed with 900 µl of 100 mM $H_3PO_4$, pH 2.5, to stop the reaction. After centrifugation, the supernatant is analyzed by HPLC as described below.

The eluent is composed of HPLC-quality acetonitrile diluted in 50 mM $H_3PO_4$ (0.9 liters of 50 mM $H_3PO_4$ mixed with 0.1 liter of acetonitrile). This eluent, which is filtered and degassed, percolates through the column with a flow rate of 1 ml/min and a pressure of 140 bar. The column used is a 5 μm C18 Nucleosil column which is 250 mm in length and 4.6 mm in diameter (INTERCHIM. Ref. N5CC18-25F). The volume injected is 5 μl and the detection is performed by reading the absorbence at a wavelength of 215 nm. Under these conditions, the HMTBM, HMTBS (2-hydroxy-4-methylthiobutanoic acid) and HMTBN (2-amino-4-methyl-thiobutanamide) peaks have respective retention times of 9 min, 11 min and 15.8 min. The amounts of HMTBN, the HMTBM and the HMTBS are deduced from the measurement of the surface area of the peaks and comparison with the surface area of the peaks of a calibration mixture of known composition.

The nitrilase activity on 2-amino-4-methyl-thiobutyronitrile is measured as follows:

A cell pellet (between 0.4 and 20 mg of DC) is resuspended in 200 mM borate buffer, pH 9.2, and incubated in a closed 2-ml tube at 30° C. for 10 minutes. The kinetics are initiated by adding a solution of AMTBN in order to obtain a final concentration of 50 mM in the reaction mixture at the start of the assay. The reaction is incubated at 30° C. with stirring. Every 15 minutes, a 50 μl sample of the suspension is withdrawn and mixed with 950 μl of the HPLC eluent (see composition below) to stop the reaction. After centrifugation, the supernatant is analyzed by HPLC as described below.

The eluent is composed of 1% of HPLC-quality acetonitrile diluted in a solution of $H_3PO_4$ at 0.5% in water. This eluent, which is filtered and degassed, percolates through the column with a flow rate of 1 ml/min. The column used is a 5 μm C18 Nucleosil column which is 250 mm in length and 4.6 mm in diameter (INTERCHIM. Ref. N5CC18-25F), maintained at a temperature of 40° C. The volume injected is 20 μl and the detection is performed by reading the absorbence at a wavelength of 210 nm. Under these conditions, the AMTBM, AMTBS (2-amino-4-methylthiobutanoic acid) and AMTBN peaks have respective retention times of 4.0 min, 4.5 min and 5.0 min. The amounts of AMTBN, the AMTBM and the AMTBS are deduced from the measurement of the surface area of the peaks and comparison with the surface area of the peaks of a calibration mixture of known composition.

The other techniques used are conventional techniques of molecular biology and microbiology, known to those skilled in the art and described, for example, by Ausubel et al., 1987 (Current Protocols in Molecular Biology, John Wiley and Sons, New. York), Maniatis et al., 1982, (Molecular Cloning: a laboratory manual. Cold Spring Harbor Laboratory, Cold Spring Harbor, N.Y.), Coligan et al., 1997 (Current Protocols in Protein Science, John Wiley & Sons, Inc).

EXAMPLES

Example 1

Construction of the Expression Plasmids pBCAT29 and pBCAT41

FIG. 2 represents the map of plasmid pRPA-BCAT41. The sites in brackets are sites which have been eliminated during cloning. Ptrp: tryptophan promoter; nitB: nitrilase gene; TrrnB: transcription terminators; end ROP: end of the gene encoding the ROP protein (Chambers et al., 1988, Gene 68: 139-149); ORI: origin of replication; RNAI/II: RNAs involved in replication (Chambers et al., mentioned above); Tc: tetracyclin resistance gene.

The 1.27 kb fragment containing the $P_{trp}$ promoter, the ribosome binding site of the λ phage cII gene (RBScII) and the nitrilase gene of *Alcaligenes faecalis* ATCC8750 (nitB) was extracted from the plasmid pRPA6BCAT6 (Application FR 96/13077) using the EcoRI and XbaI restriction enzymes, in order to be cloned into the vector pXL642 (described in CIP application Ser. No. 08/194,588) opened with the same restriction enzymes. The resulting plasmid, pRPA-BCAT15, was opened with the StuI and BsmI enzymes and the 4.3 kb fragment was ligated with the 136 bp StuI-BsmI fragment purified from pRPA-BCAT4 (Application FR 96/13077), to produce the plasmid pRPA-BCAT19. The partial sequencing of pRPA-BCAT19 confirmed the replacement of the codon of the Asp279 residue of the nitrilase with the codon of an Asn279 residue. The 1.2 kb EcoRI-XbaI fragment of pRPA-BCAT19 containing the $P_{trp}$::RBScII::nitB fusion was then cloned into the vector pRPA-BCAT28 opened with the same enzymes, to produce the 6.2 kb plasmid pRPA-BCAT29. The vector pRPA-BCAT28 was obtained by ligating the 3.9 kb SspI-ScaI fragment of pXL642 (CIP, application Ser. No. 08/194,588) with the 2.1 kb SmaI fragment of pHP45ΩTc (Fellay et al., 1987, Gene 52: 147-154) in order to replace the ampicillin resistance marker with the tetracycline resistance marker. Destruction of the NdeI site close to the origin of replication of the plasmid pRPA-BCAT29 by partial NdeI digestion and the action of *E. coli* Polymerase I (Klenow fragment) produced the plasmid pRPA-BCAT41, a map of which is represented in FIG. 2.

Removal of the 0.55 bp Xcm1 fragment from the plasmid pRPA-BCAT41 by Xcm1 digestion and ligation produced the plasmid pRPA-BCAT72.

Example 2

Replacement of Cysteine 162 of NitB with an Asparagine

The codon of cysteine 162 of the nitB gene was modified by site-directed mutagenesis using the primers NitB162 (SEQ ID NO: 1 CGCGTCGGTGCCCTGMASTGCTGG-GAGC in which M=A/C and S=G/C) and SR (SEQ ID NO: 2 CGGCAATGATCAGGCCTTCGGC).

An internal 361 bp fragment was amplified by PCR reaction using the primers NitB162, and SR, the matrix pRPA-BCAT41, the Pwo polymerase (Boehringer) and the following incubation program: 5 min at 95° C., five cycles (one minute at 95° C., 1 min at 58° C., 1 min at 72° C.), 35 cycles (45 seconds at 95° C., 30 seconds at 58° C., 30 seconds at 72° C.), 5 min at 72° C.

After purification of the amplified fragment by migration on an agarose gel, and extraction of the fragment using the QIAEX gel extraction kit (Qiagen), the DNA was incubated in the presence of the StuI and BanI restriction enzymes (New England Biolabs) at 37° C. for 16 hours in a buffer recommended by the supplier. Another internal fragment, of 498 bp, was amplified in a similar manner using the primers PCRAF1 (described in Application FR 96/13072) and NitB1 (SEQ ID NO: 3 GCAGCACAGGGCACCGACGC).

After purification of the amplified fragment by migration on agarose gel, and extraction of the fragment using the QIAEX gel extraction kit (Qiagen), the DNA was incubated in the presence of the NdeI and BanI restriction enzymes (New England Biolabs) at 37° C. for 16 h in a buffer recommended by the supplier.

The vector pRPA-BCAT72 was opened with the NdeI and StuI enzymes and the 5.43 kp fragment was purified on agarose gel and extracted using the QIAEX gel extraction kit (Qiagen).

The three fragments described above were then ligated and the ligation mixture was introduced into the *E. coli* strain DH5alpha by electroporation. The clones obtained were analyzed by restriction with the EcoRI and XbaI enzymes in order to select plasmids having a 1.26 kb insert. After sequencing the region encompassing codon 162 of the nitrilase gene, 2 plasmids carrying the desired codon (AAC instead of TGC) were selected and named pRPA-BCAT75.

These plasmids were introduced into the *E. coli* strain RPA-BIOCAT496, to give the strains RPA-BIOCAT526 and 527. The RPA-BIOCAT496 strain corresponds to the W strain (ATCC9637) into which the plasmid pRPA-BCAT34 has previously been introduced. The plasmid pRPA-BCAT34 corresponds to the plasmid pXL2035 (Lévy-Schil et al., 1995, Gene 161: 15-20) into which a 475 bp fragment carrying the trpR gene encoding the regulator of the Ptrp promoter has been cloned between the EcoRI and NotI sites. This fragment was extracted from the plasmid pRPA-BCAT30, constructed by cloning into the vector pSL301 (Brosius, 1989, DNA 8: 759-777) a 434 bp AatII-StuI fragment carrying the trpR gene and its promoter extracted from the plasmid pRPG9 (Gunsalus and Yanofsky, 1980, Proc. Natl. Acad. Sci. USA 77: 7117-7121).

Example 3

Influence of the Cysteine 162 of NitB on the Selectivity of the Nitrilase During Hydrolysis of HMTBN The RPA-BIOCAT526, RPA-BIOCAT527 and RPA-BIOCAT497 strains (corresponding to the RPA-BIOCAT496 strain into which the plasmid pRPA-BCAT41 has previously been introduced) were cultured under the conditions described in example 5 of Application FR 96/13072, with the following modifications: preculturing for 8 h, seeding at 1:50 into M9 glucose medium containing 0.4% of casamino acids, 12 μg/ml of tetracycline and 50 μg/ml of kanamycin.

The nitrilase activity of HMTBN was measured on a cell pellet washed in 100 mM potassium phosphate buffer, pH 7, as described above, using 1 mg of DC in a reaction volume of 1 ml. The selectivity of the strains was measured after 2 hours of hydrolysis, relating the surface area of the peak of amide formed to the sum of the surface areas of the peaks of amide and of acid formed. It is expressed as a percentage. The results are given in table 1:

TABLE 1

Selectivity of strains 526, 527 and 497

| RPA-BIOCAT | Activity (μmol/h.mgDC[1]) | Selectivity |
|---|---|---|
| 497 | 65 | 0.04% |
| 526 | 76 | 0.2% |
| 527 | 65 | 0.2% |

[1]mg DC: weight of dry cells estimated from the optical density of the sample at 660 nm, $OD_{660}$ (mg DC = $OD_{660}$ × 0.35)

These results show that substituting cysteine 162 with an asparagine modifies the selectivity of NitB for the hydrolysis of HMTBN.

Example 4

Replacement of the Glutamine 162 of NitA with a Cysteine

The codon of glutamine 162 of the NitA nitrilase was modified to a cysteine codon by site-directed mutagenesis using the QuickChange™ site-directed mutagenesis kit (Stratagene).

The primers NitA 163 (SEQ ID NO. 4 GCATGTTC-CCAGCAGCAGAGTCCCCCAAGATTCC) and NitA 162 (SEQ ID NO. 5 GGAATCTTGGGGGACTCTGCT-GCTGGGAACATGC) were used under the conditions recommended by the supplier, on DNA of the plasmid pXL2158 (Lévy-Schil et al., 1995, Gene 161: 15-20).

The incubation program for the PCR reaction comprised 30 seconds at 95° C. and 16 cycles of 30 seconds at 95° C.-1 minute at 55° C.-12 minutes at 68° C. After digesting the DNA with DpnI and transforming *E. coli* XL1-BLUE competent cells (Stratagene) with 1 μl of the reaction mixture, the clones obtained were analyzed by plasmid restriction profile using the BpmI enzyme. Since the mutation introduced modifies a BpmI restriction site, five clones which have lost one of the 3 BpmI sites were selected. The plasmids which they contained were introduced, separately, into the RPA-BIOCAT496 strain, to give the strains RPA-BIOCAT570 to RPA-BIOCAT574.

Example 5

Modulation of the Selectivity of NitA C162 for the Hydrolysis of HMTBN after Substitution with a Cysteine at Position 162

The plasmid pXL2158 was introduced into the RPA-BIOCAT496 strain to give the RPA-BIOCAT575 strain. The strains RPA-BIOCAT570 to RPA-BIOCAT575 were cultured under the expression conditions described above, replacing tetracycline with ampicillin at 100 μg/ml. The nitrilase activity of these strains was assayed as described above, using 5 mg of cells (as dry weight estimated from the $OD_{660}$) in a reaction volume of 1 ml and for 1 hour. The selectivity is measured by calculating the ratio of the surface area of the peak corresponding to the amide to the surface area of the peak corresponding to the acid. It is expressed as a percentage. Table 2 gives the results.

TABLE 2

Selectivity of the strains RPA-BIOCAT570 to 575 on HMTBN

| RPA-BIOCAT | Activity (mmol/h.g DC) | Selectivity |
|---|---|---|
| 575 | 135 | 17% |
| 570 | 8 | 4.3 |
| 571 | 8 | 4.3 |
| 572 | 4 | 4.5 |
| 573 | 7 | 4.4 |
| 574 | 4 | 4.5 |

These results show that substituting glutamine 162 of NitA with a cysteine allows a 4-fold modulation of selectivity for the hydrolysis of HMTBN.

Example 6

Modulation of the Selectivity of NitA for the Hydrolysis of AMTBN after Substitution with a Cysteine at Position 162

The RPA-BIOCAT570 and RPA-BIOCAT575 strains were cultured under the expression conditions described above. The nitrilase activity of these strains was assayed using 2-amino-4-methylthiobutanenitrile or AMTBN ($C_5H_{10}N_2S$) as substrate, at 50 mM in borate buffer, pH 9.2. The equivalent of 10 mg of RPA-BIOCAT570 cells (expressed as dry weight) and of 0.4 mg of RPA-BIOCAT575 cells (expressed as dry weight) were used at 30° C. for 24 h in a reaction volume of 1 ml. The production of AMTBS and AMTBA were measured by HPLC as described above and the selectivity was calculated in a similar manner. The results are given in table 3.

TABLE 3

Selectivity of the RPA-BIOCAT570 and 575 strains on AMTBN

| RPA-BIOCAT | Assay number | Activity (mmol/h.g DC)[1] | TT[2] at 24 h | Selectivity |
| --- | --- | --- | --- | --- |
| 575 | 1 | 43 | 98 | 6.3 |
| 575 | 2 | 50 | 100 | 5.6 |
| 570 | 3 | 1.5 | 100 | 1.0 |
| 570 | 2 | 2.7 | 97 | 0.6 |

[1]Activity measured after 30 minutes of hydrolysis
[2]TT: (initial amount of AMTBN - amount of AMTBN at 24 h/initial amount of AMTBN at 24 h/initial amount of AMTBN These results show that substituting glutamine 162 of NitA with cysteine allows a 4-fold modulation of selectivity on a substrate other than HMTBN, in this case AMTBN.

Example 7

Other Substitution at Position 162 on NitB and Modulation of Selectivity on HMTBN By sequencing the region encompassing codon 162 of the nitB gene harbored by the clones derived from the mutagenesis described in example 2, it was possible to identify clones carrying the CAG codon instead of TGC at position 162. The corresponding plasmids were named pRPA-BCAT78 and carry a nitB insert encoding a nitrilase NitB Q162, in which cysteine 162 is substituted with a glutamine. These plasmids were introduced into the E. coli strain RPA-BIOCAT496, to give the strains RPA-BIOCAT530 and 531. The RPA-BIOCAT530, RPA-BIOCAT531 and RPA-BIOCAT497 strains were cultured under the conditions described in example 3. The nitrilase activity on HMTBN was measured on a cell pellet washed in 100 mM potassium phosphate buffer, pH 7, as described in example 4 of Application FR 96/13072, using 1 mg of DC in a reaction volume of 1 ml. The selectivity of the strains was measured after 2 hours of hydrolysis, relating the molar amount of amide formed to the sum of the molar amounts of amide and of acid formed. It is expressed as a percentage. The results are given in Table 4:

TABLE 4

Selectivity of strains 530, 531 and 497

| RPA-BIOCAT | Activity (μmol/h.mg DC[1]) | Selectivity |
| --- | --- | --- |
| 497 | 65 | 0.04% |
| 530 | 18 | 0.2% |
| 531 | 22 | 0.2% |

[1]mg DC: weight of dry cells estimated from the optical density of the sample at 660 nm, $OD_{660}$ (mg DC = $OD_{660}$ × 0.35)

These results show that substituting cysteine with a glutamine modifies the selectivity of NitB the hydrolysis of HMTBN.

---

The invention claimed is:

1. A method for modulating nitrilase selectivity of a nitrilase enzyme chosen from the group consisting of nitrilase p Athalia 1 of *Arabidopsis thaliana* (SEQ ID NO: 6), nitrilase p Athalia 2 of *Arabidopsis thaliana* (SEQ ID NO: 7), nitrilase p Athalia 3 of *Arabidopsis thaliana* (SEQ ID NO: 8), nitrilase p Athalia 4 of *Arabidopsis thaliana* (SEQ ID NO: 12), nitrilase p Tobacco 1 of *Nicotiana tabacum* (SEQ ID NO: 9), nitrilase p Tobacco 2 of *Nicotiana tabacum* (SEQ ID NO: 10), nitrilase b RhodocJ1 of *Rhodococcus rhodocrous* J1 (SEQ ID NO: 13), nitrilase b RrhodoPA3 of *Rhodococcus rhodocrous* PA34 (SEQ ID NO: 14), nitrilase b RrhodocK22 of *Rhodococcus rhodocrous* K22 (SEQ ID NO: 16), nitrilase b Kozaenae of *Klebsiella ozaenae* (SEQ ID NO: 17) and nitrilase NitA of *Comamonas testosteroni* (SEQ ID NO: 18), wherein nitrilase selectivity is defined as the percentage of compounds not having a carboxylic function that are released by the nitrilase-catalyzed hydrolysis of a nitrile, comprising replacing the amino acid corresponding to position 162 of SEQ ID NO: 19 (primary sequence of nitrilase NitB of *Alcaligenes faecalis*) in the nitrilase with a cysteine, wherein the amino acid corresponding to position 162 of SEQ ID NO: 19 in the nitrilase prior to replacement is not cysteine.

2. The method of claim 1 wherein the percentage of compounds not having a carboxylic function that are released by the nitrilase-catalyzed hydrolysis of a nitrile is decreased.

3. The method of claim 1 wherein the nitrilase selectivity of the nitrilase NitA of *Comamonas testosteroni* (SEQ ID NO: 18) is modulated.

* * * * *

SEQUENCE LISTING

```
<160> NUMBER OF SEQ ID NOS: 20

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgcgtcggtg ccctgmastg ctgggagc                                        28

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
```
cggcaatgat caggccttcg gc                                                    22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcagcacagg gcaccgacgc                                                       20

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcatgttccc agcagcagag tcccccaaga ttcc                                       34

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggaatcttgg gggactctgc tgctgggaac atgc                                       34

<210> SEQ ID NO 6
<211> LENGTH: 346
<212> TYPE: PRT
<213> ORGANISM: Arabidopsis thaliana

<400> SEQUENCE: 6

Met Ser Ser Thr Lys Asp Met Ser Thr Val Gln Asn Ala Thr Pro Phe
  1               5                  10                  15

Asn Gly Val Ala Pro Ser Thr Thr Val Arg Val Thr Ile Val Gln Ser
                 20                  25                  30

Ser Thr Val Tyr Asn Asp Thr Pro Ala Thr Ile Asp Lys Ala Glu Lys
             35                  40                  45

Tyr Ile Val Glu Ala Ala Ser Lys Gly Ala Glu Leu Val Leu Phe Pro
         50                  55                  60

Glu Gly Phe Ile Gly Gly Tyr Pro Arg Gly Phe Arg Phe Gly Leu Ala
 65                  70                  75                  80

Val Gly Val His Asn Glu Glu Gly Arg Asp Glu Phe Arg Lys Tyr His
                 85                  90                  95

Ala Ser Ala Ile His Val Pro Gly Pro Glu Val Ala Arg Leu Ala Asp
            100                 105                 110

Val Ala Arg Lys Asn His Val Tyr Leu Val Met Gly Ala Ile Glu Lys
        115                 120                 125

Glu Gly Tyr Thr Leu Tyr Cys Thr Val Leu Phe Phe Ser Pro Gln Gly
    130                 135                 140

Gln Phe Leu Gly Lys His Arg Lys Leu Met Pro Thr Ser Leu Glu Arg
145                 150                 155                 160

```
Cys Ile Trp Gly Gln Gly Asp Gly Ser Thr Ile Pro Val Tyr Asp Thr
                165                 170                 175

Pro Ile Gly Lys Leu Gly Ala Ala Ile Cys Trp Glu Asn Arg Met Pro
            180                 185                 190

Leu Tyr Arg Thr Ala Leu Tyr Ala Lys Gly Ile Glu Leu Tyr Cys Ala
        195                 200                 205

Pro Thr Ala Asp Gly Ser Lys Glu Trp Gln Ser Ser Met Leu His Ile
210                 215                 220

Ala Ile Glu Gly Gly Cys Phe Val Leu Ser Ala Cys Gln Phe Cys Gln
225                 230                 235                 240

Arg Lys His Phe Pro Asp His Pro Asp Tyr Leu Phe Thr Asp Trp Tyr
                245                 250                 255

Asp Asp Lys Glu His Asp Ser Ile Val Ser Gln Gly Gly Ser Val Ile
            260                 265                 270

Ile Ser Pro Leu Gly Gln Val Leu Ala Gly Pro Asn Phe Glu Ser Glu
        275                 280                 285

Gly Leu Val Thr Ala Asp Ile Asp Leu Gly Asp Ile Ala Arg Ala Lys
290                 295                 300

Leu Tyr Phe Asp Ser Val Gly Tyr Tyr Ser Arg Pro Asp Val Leu His
305                 310                 315                 320

Leu Thr Val Asn Glu His Pro Arg Lys Ser Val Thr Phe Val Thr Lys
                325                 330                 335

Val Glu Lys Ala Glu Asp Asp Ser Asn Lys
            340                 345

<210> SEQ ID NO 7
<211> LENGTH: 339
<212> TYPE: PRT
<213> ORGANISM: Arabidopsis thaliana

<400> SEQUENCE: 7

Met Ser Thr Ser Glu Asn Thr Pro Phe Asn Gly Val Ala Ser Ser Thr
  1               5                  10                  15

Ile Val Arg Ala Thr Ile Val Gln Ala Ser Thr Val Tyr Asn Asp Thr
             20                  25                  30

Pro Ala Thr Leu Glu Lys Ala Asn Lys Phe Ile Val Glu Ala Ala Ser
         35                  40                  45

Lys Gly Ser Glu Leu Val Val Phe Pro Glu Ala Phe Ile Gly Gly Tyr
     50                  55                  60

Pro Arg Gly Phe Arg Phe Gly Leu Gly Val Gly Val His Asn Glu Glu
 65                  70                  75                  80

Gly Arg Asp Glu Phe Arg Lys Tyr His Ala Ser Ala Ile Lys Val Pro
                 85                  90                  95

Gly Pro Glu Val Glu Lys Leu Ala Glu Leu Ala Gly Lys Asn Asn Val
            100                 105                 110

Tyr Leu Val Met Gly Ala Ile Glu Lys Asp Gly Tyr Thr Leu Tyr Cys
        115                 120                 125

Thr Ala Leu Phe Phe Ser Pro Gln Gly Gln Phe Leu Gly Lys His Arg
130                 135                 140

Lys Leu Met Pro Thr Ser Leu Glu Arg Cys Ile Trp Gly Gln Gly Asp
145                 150                 155                 160

Gly Ser Thr Ile Pro Val Tyr Asp Thr Pro Ile Gly Lys Leu Gly Ala
                165                 170                 175

Ala Ile Cys Trp Glu Asn Arg Met Pro Leu Tyr Arg Thr Ala Leu Tyr
            180                 185                 190
```

```
Ala Lys Gly Ile Glu Leu Tyr Cys Ala Pro Thr Ala Asp Gly Ser Lys
        195                 200                 205

Glu Trp Gln Ser Ser Met Leu His Ile Ala Ile Glu Gly Gly Cys Phe
    210                 215                 220

Val Leu Ser Ala Cys Gln Phe Cys Leu Arg Lys Asp Phe Pro Asp His
225                 230                 235                 240

Pro Asp Tyr Leu Phe Thr Asp Trp Tyr Asp Asp Lys Glu Pro Asp Ser
                245                 250                 255

Ile Val Ser Gln Gly Gly Ser Val Ile Ser Pro Leu Gly Gln Val
                260                 265                 270

Leu Ala Gly Pro Asn Phe Glu Ser Glu Gly Leu Ile Thr Ala Asp Leu
            275                 280                 285

Asp Leu Gly Asp Val Ala Arg Ala Lys Leu Tyr Phe Asp Ser Val Gly
    290                 295                 300

His Tyr Ser Arg Pro Asp Val Leu His Leu Thr Val Asn Glu His Pro
305                 310                 315                 320

Lys Lys Pro Val Thr Phe Ile Ser Lys Val Glu Lys Ala Glu Asp Asp
                325                 330                 335

Ser Asn Lys

<210> SEQ ID NO 8
<211> LENGTH: 346
<212> TYPE: PRT
<213> ORGANISM: Arabidopsis thaliana

<400> SEQUENCE: 8

Met Ser Ser Thr Glu Glu Met Ser Ser Val Lys Asn Thr Thr Gln Val
1               5                   10                  15

Ile Gly Val Asp Pro Ser Ser Thr Val Arg Val Thr Ile Val Gln Ser
                20                  25                  30

Ser Thr Val Tyr Asn Asp Thr Pro Ala Thr Leu Asp Lys Ala Glu Lys
            35                  40                  45

Phe Ile Val Glu Ala Ala Ser Lys Gly Ala Lys Leu Val Leu Phe Pro
    50                  55                  60

Glu Ala Phe Ile Gly Gly Tyr Pro Arg Gly Phe Arg Phe Gly Leu Ala
65                  70                  75                  80

Val Gly Val His Asn Glu Glu Gly Arg Asp Glu Phe Arg Asn Tyr His
                85                  90                  95

Ala Ser Ala Ile Lys Val Pro Gly Pro Glu Val Glu Arg Leu Ala Glu
            100                 105                 110

Leu Ala Gly Lys Asn Asn Val His Leu Val Met Gly Ala Ile Glu Lys
        115                 120                 125

Asp Gly Tyr Thr Leu Tyr Cys Thr Ala Leu Phe Phe Ser Pro Gln Gly
    130                 135                 140

Gln Phe Leu Gly Lys His Arg Lys Val Met Pro Thr Ser Leu Glu Arg
145                 150                 155                 160

Cys Ile Trp Gly Gln Gly Asp Gly Ser Thr Ile Pro Val Tyr Asp Thr
                165                 170                 175

Pro Ile Gly Lys Ile Gly Ala Ala Ile Cys Trp Glu Asn Arg Met Pro
            180                 185                 190

Leu Tyr Arg Thr Ala Leu Tyr Ala Lys Gly Ile Glu Ile Tyr Cys Ala
        195                 200                 205

Pro Thr Ala Asp Tyr Ser Leu Glu Trp Gln Ala Ser Met Ile His Ile
    210                 215                 220
```

```
Ala Val Glu Gly Gly Cys Phe Val Leu Ser Ala His Gln Phe Cys Lys
225                 230                 235                 240

Arg Arg Glu Phe Pro Glu His Pro Asp Tyr Leu Phe Asn Asp Ile Val
            245                 250                 255

Asp Thr Lys Glu His Asp Pro Thr Val Ser Gly Gly Gly Ser Val Ile
            260                 265                 270

Ile Ser Pro Leu Gly Lys Val Leu Ala Gly Pro Asn Tyr Glu Ser Glu
            275                 280                 285

Gly Leu Val Thr Ala Asp Leu Asp Leu Gly Asp Ile Ala Arg Ala Lys
            290                 295                 300

Leu Tyr Phe Asp Val Val Gly His Tyr Ser Lys Pro Asp Ile Phe Asn
305                 310                 315                 320

Leu Thr Val Asn Glu His Pro Lys Lys Pro Val Thr Phe Met Thr Lys
                325                 330                 335

Val Glu Lys Ala Glu Asp Glu Ser Asn Lys
            340                 345

<210> SEQ ID NO 9
<211> LENGTH: 349
<212> TYPE: PRT
<213> ORGANISM: Nicotiana tabacum

<400> SEQUENCE: 9

Met Ala Leu Val Pro Thr Pro Ala Val Asn Glu Gly Pro Leu Phe Ala
1               5                   10                  15

Glu Val Asp Met Gly Asp Asn Ser Ser Thr Pro Thr Val Arg Ala Thr
            20                  25                  30

Val Val Gln Ala Ser Thr Ile Phe Tyr Asp Thr Pro Ala Thr Leu Val
        35                  40                  45

Lys Ala Glu Arg Leu Leu Ala Glu Ala Ala Ser Tyr Gly Ala Gln Leu
    50                  55                  60

Val Val Phe Pro Glu Ala Phe Ile Gly Gly Tyr Pro Arg Gly Ser Thr
65                  70                  75                  80

Phe Gly Val Ser Ile Gly Asn Arg Thr Ala Lys Gly Lys Glu Glu Phe
                85                  90                  95

Arg Lys Tyr His Ala Ser Ala Ile Asp Val Pro Gly Pro Glu Val Asp
            100                 105                 110

Arg Leu Ala Ala Met Ala Gly Lys Tyr Lys Val Tyr Leu Val Met Gly
        115                 120                 125

Val Ile Glu Arg Asp Gly Tyr Thr Leu Tyr Cys Thr Val Leu Phe Phe
130                 135                 140

Asp Ser Gln Gly His Phe Leu Gly Lys His Arg Lys Ile Met Pro Thr
145                 150                 155                 160

Ala Leu Glu Arg Ile Ile Trp Gly Phe Gly Asp Gly Ser Thr Ile Pro
            165                 170                 175

Val Tyr Asp Thr Pro Leu Gly Lys Ile Gly Ala Ala Ile Cys Trp Glu
        180                 185                 190

Asn Arg Met Pro Leu Leu Arg Thr Ala Met Tyr Ala Lys Gly Ile Glu
    195                 200                 205

Ile Tyr Cys Ala Pro Thr Ala Asp Ser Arg Asp Val Trp Gln Ala Ser
210                 215                 220

Met Thr His Ile Ala Leu Glu Gly Gly Cys Phe Val Leu Ser Ala Asn
225                 230                 235                 240

Gln Phe Cys Arg Arg Lys Asp Tyr Pro Pro Pro Glu Tyr Val Phe
```

```
                    245                 250                 255
Ser Gly Thr Glu Glu Asp Leu Thr Pro Asp Ser Ile Val Cys Ala Gly
            260                 265                 270

Gly Ser Val Ile Ile Ser Pro Ser Gly Ala Val Leu Ala Gly Pro Asn
            275                 280                 285

Tyr Val Gly Glu Ala Leu Ile Ser Ala Asp Leu Asp Leu Gly Glu Ile
            290                 295                 300

Ala Arg Ala Lys Phe Asp Phe Asp Val Val Gly His Tyr Ala Arg Pro
305                 310                 315                 320

Glu Val Leu Ser Leu Ile Val Arg Asp His Ala Val Ser Pro Val Ser
            325                 330                 335

Phe Thr Ser Thr Ser Ser Lys Ala Glu Ser Ser Pro Lys
            340                 345

<210> SEQ ID NO 10
<211> LENGTH: 348
<212> TYPE: PRT
<213> ORGANISM: Nicotiana tabacum

<400> SEQUENCE: 10

Met Ala Leu Val Pro Thr Pro Val Val Asn Glu Gly Pro Met Phe Ala
  1               5                  10                  15

Glu Val Asp Met Gly Asp Asn Ser Ser Thr Pro Thr Val Arg Ala Thr
             20                  25                  30

Val Val Gln Ala Ser Thr Ile Phe Tyr Asp Thr Pro Ala Thr Leu Asp
             35                  40                  45

Lys Ala Glu Arg Leu Leu Ala Glu Ala Ser Tyr Gly Ala Gln Leu
         50                  55                  60

Val Val Phe Pro Glu Ala Phe Ile Gly Gly Tyr Pro Arg Gly Ser Thr
 65                  70                  75                  80

Phe Gly Val Ser Ile Gly Asn Arg Thr Ala Lys Gly Lys Glu Glu Phe
                 85                  90                  95

Arg Lys Tyr His Ala Ser Ala Ile Asp Val Pro Gly Pro Glu Val Asp
            100                 105                 110

Arg Leu Ala Ala Met Ala Gly Lys Tyr Lys Val Tyr Leu Val Met Gly
            115                 120                 125

Val Ile Glu Arg Asp Gly Tyr Thr Leu Tyr Cys Thr Val Leu Phe Phe
            130                 135                 140

Asp Ser Gln Gly His Tyr Leu Gly Lys His Arg Lys Ile Met Pro Thr
145                 150                 155                 160

Ala Leu Glu Arg Ile Ile Trp Gly Phe Gly Asp Gly Ser Thr Ile Pro
            165                 170                 175

Val Tyr Asp Thr Pro Leu Gly Lys Ile Gly Ala Ala Ile Cys Trp Glu
            180                 185                 190

Asn Arg Met Pro Leu Leu Arg Thr Ala Met Tyr Ala Lys Gly Ile Glu
            195                 200                 205

Ile Tyr Cys Ala Pro Thr Ala Asp Ser Arg Asp Val Trp Gln Ala Ser
            210                 215                 220

Met Thr His Ile Ala Leu Glu Gly Gly Cys Phe Val Leu Ser Ala Asn
225                 230                 235                 240

Gln Phe Cys Arg Arg Lys Asp Tyr Pro Pro Pro Glu Tyr Val Phe
            245                 250                 255

Ser Gly Thr Glu Asp Leu Thr Pro Asp Ser Ile Val Cys Ala Gly Gly
            260                 265                 270
```

```
Ser Val Ile Ile Ser Pro Ser Gly Ala Val Leu Ala Gly Pro Asn Tyr
        275                 280                 285

Glu Gly Glu Ala Leu Ile Ser Ala Asp Leu Asp Leu Gly Glu Ile Ala
        290                 295                 300

Arg Ala Lys Phe Asp Phe Asp Val Val Gly His Tyr Ala Arg Pro Glu
305                 310                 315                 320

Val Leu Ser Leu Ile Val Arg Asp His Ala Val Ser Pro Val Ser Phe
                325                 330                 335

Thr Ser Thr Ser Ser Lys Ala Glu Ser Ser Pro Lys
                340                 345

<210> SEQ ID NO 11
<211> LENGTH: 362
<212> TYPE: PRT
<213> ORGANISM: Oryza sativa

<400> SEQUENCE: 11

Met Ala Met Val Pro Ser Gly Ser Gly Gly Pro Pro Val Ile Ala
  1               5                  10                  15

Glu Val Glu Met Asn Gly Gly Ala Thr Ser Gly Ala Ala Thr Val Arg
                 20                  25                  30

Ala Thr Val Val Gln Ala Ser Thr Val Phe Tyr Asp Thr Pro Ala Thr
             35                  40                  45

Leu Asp Lys Ala Glu Arg Leu Ile Glu Glu Ala Ala Gly Tyr Gly Ser
         50                  55                  60

Gln Leu Val Val Phe Pro Glu Ala Phe Val Gly Gly Tyr Pro Arg Gly
 65                  70                  75                  80

Ser Thr Phe Gly Phe Gly Ala Asn Ile Ser Ile Gly Asn Pro Lys Asp
                 85                  90                  95

Lys Gly Lys Glu Glu Phe Arg Lys Tyr His Ala Ala Ala Ile Glu Val
                100                 105                 110

Pro Gly Pro Glu Val Thr Arg Leu Ala Ala Met Ala Gly Lys Tyr Lys
            115                 120                 125

Val Phe Leu Val Met Gly Val Ile Glu Arg Glu Gly Tyr Thr Leu Tyr
        130                 135                 140

Cys Ser Val Leu Phe Phe Asp Pro Leu Gly Arg Tyr Leu Gly Lys His
145                 150                 155                 160

Arg Lys Leu Met Pro Thr Ala Leu Glu Arg Ile Ile Trp Gly Phe Gly
                165                 170                 175

Asp Gly Ser Thr Ile Pro Val Tyr Asp Thr Pro Leu Gly Lys Ile Gly
            180                 185                 190

Ala Leu Ile Cys Trp Glu Asn Lys Met Pro Leu Leu Arg Thr Ala Leu
        195                 200                 205

Tyr Gly Lys Gly Ile Glu Ile Tyr Cys Ala Pro Thr Ala Asp Ser Arg
210                 215                 220

Gln Val Trp Gln Ala Ser Met Thr His Ile Ala Leu Glu Gly Gly Cys
225                 230                 235                 240

Phe Val Leu Ser Ala Asn Gln Phe Cys Arg Arg Lys Asp Tyr Pro Pro
                245                 250                 255

Pro Pro Glu Tyr Val Phe Thr Gly Leu Gly Glu Glu Pro Ser Pro Asp
            260                 265                 270

Thr Val Val Cys Pro Gly Gly Ser Val Ile Ile Ser Pro Ser Gly Glu
        275                 280                 285

Val Leu Ala Gly Pro Asn Tyr Glu Gly Glu Ala Leu Ile Thr Ala Asp
    290                 295                 300
```

```
Leu Asp Leu Gly Glu Ile Val Arg Ala Lys Phe Asp Phe Asp Val Val
305                 310                 315                 320

Gly His Tyr Ala Arg Pro Glu Val Leu Ser Leu Val Val Asn Asp Gln
                325                 330                 335

Pro His Leu Pro Val Ser Phe Thr Ser Ala Ala Glu Lys Thr Thr Ala
            340                 345                 350

Ala Lys Ser Asp Ser Thr Ala Lys Pro Tyr
        355                 360

<210> SEQ ID NO 12
<211> LENGTH: 355
<212> TYPE: PRT
<213> ORGANISM: Arabidopsis thaliana

<400> SEQUENCE: 12

Met Ser Met Gln Gln Glu Thr Ser His Met Thr Ala Ala Pro Gln Thr
1               5                   10                  15

Asn Gly His Gln Ile Phe Pro Glu Ile Asp Met Ser Ala Gly Asp Ser
            20                  25                  30

Ser Ser Ile Val Arg Ala Thr Val Val Gln Ala Ser Thr Val Phe Tyr
        35                  40                  45

Asp Thr Pro Ala Thr Leu Asp Lys Ala Glu Arg Leu Leu Ser Glu Ala
    50                  55                  60

Ala Glu Asn Gly Ser Gln Leu Val Val Phe Pro Glu Ala Phe Ile Gly
65                  70                  75                  80

Gly Tyr Pro Arg Gly Ser Thr Phe Glu Leu Ala Ile Gly Ser Arg Thr
                85                  90                  95

Ala Lys Gly Arg Asp Asp Phe Arg Lys Tyr His Ala Ser Ala Ile Asp
            100                 105                 110

Val Pro Gly Pro Glu Val Glu Arg Leu Ala Leu Met Ala Lys Lys Tyr
        115                 120                 125

Lys Val Tyr Leu Val Met Gly Val Ile Glu Arg Glu Gly Tyr Thr Leu
    130                 135                 140

Tyr Cys Thr Val Leu Phe Phe Asp Ser Gln Gly Leu Phe Leu Gly Lys
145                 150                 155                 160

His Arg Lys Leu Met Pro Thr Ala Leu Glu Arg Cys Ile Trp Gly Phe
                165                 170                 175

Gly Asp Gly Ser Thr Ile Pro Val Phe Asp Thr Pro Ile Gly Lys Ile
            180                 185                 190

Gly Ala Ala Ile Cys Trp Glu Asn Arg Met Pro Ser Leu Arg Thr Ala
        195                 200                 205

Met Tyr Ala Lys Gly Ile Glu Ile Tyr Cys Ala Pro Thr Ala Asp Ser
    210                 215                 220

Arg Glu Thr Trp Leu Ala Ser Met Thr His Ile Ala Leu Glu Gly Gly
225                 230                 235                 240

Cys Phe Val Leu Ser Ala Asn Gln Phe Cys Arg Arg Lys Asp Tyr Pro
                245                 250                 255

Ser Pro Pro Glu Tyr Met Phe Ser Gly Ser Glu Ser Leu Thr Pro
            260                 265                 270

Asp Ser Val Val Cys Ala Gly Ser Ser Ile Ile Ser Pro Leu Gly
        275                 280                 285

Ile Val Leu Ala Gly Pro Asn Tyr Arg Gly Glu Ala Leu Ile Thr Ala
    290                 295                 300

Asp Leu Asp Leu Gly Asp Ile Ala Arg Ala Lys Phe Asp Phe Asp Val
```

```
             305                 310                 315                 320
Val Gly His Tyr Ser Arg Pro Glu Val Phe Ser Leu Asn Ile Arg Glu
                325                 330                 335

His Pro Arg Lys Ala Val Ser Phe Lys Thr Ser Lys Val Met Glu Asp
                340                 345                 350

Glu Ser Val
        355

<210> SEQ ID NO 13
<211> LENGTH: 366
<212> TYPE: PRT
<213> ORGANISM: Rhodococcus rhodochrous

<400> SEQUENCE: 13

Met Val Glu Tyr Thr Asn Thr Phe Lys Val Ala Ala Val Gln Ala Gln
  1               5                  10                  15

Pro Val Trp Phe Asp Ala Ala Lys Thr Val Asp Lys Thr Val Ser Ile
                 20                  25                  30

Ile Ala Glu Ala Ala Arg Asn Gly Cys Glu Leu Val Ala Phe Pro Glu
             35                  40                  45

Val Phe Ile Pro Gly Tyr Pro Tyr His Ile Trp Val Asp Ser Pro Leu
         50                  55                  60

Ala Gly Met Ala Lys Phe Ala Val Arg Tyr His Glu Asn Ser Leu Thr
 65                  70                  75                  80

Met Asp Ser Pro His Val Gln Arg Leu Leu Asp Ala Ala Arg Asp His
                 85                  90                  95

Asn Ile Ala Val Val Val Gly Ile Ser Glu Arg Asp Gly Gly Ser Leu
            100                 105                 110

Tyr Met Thr Gln Leu Val Ile Asp Ala Asp Gly Gln Leu Val Ala Arg
        115                 120                 125

Arg Arg Lys Leu Lys Pro Thr His Val Glu Arg Ser Val Tyr Gly Glu
    130                 135                 140

Gly Asn Gly Ser Asp Ile Ser Val Tyr Asp Met Pro Phe Ala Arg Leu
145                 150                 155                 160

Gly Ala Leu Asn Cys Trp Glu His Phe Gln Thr Leu Thr Lys Tyr Ala
                165                 170                 175

Met Tyr Ser Met His Glu Gln Val His Val Ala Ser Trp Pro Gly Met
            180                 185                 190

Ser Leu Tyr Gln Pro Glu Val Pro Ala Phe Gly Val Asp Ala Gln Leu
        195                 200                 205

Thr Ala Thr Arg Met Tyr Ala Leu Glu Gly Gln Thr Phe Val Val Cys
    210                 215                 220

Thr Thr Gln Val Val Thr Pro Glu Ala His Glu Phe Phe Cys Asp Asn
225                 230                 235                 240

Asp Glu Gln Arg Lys Leu Ile Gly Arg Gly Gly Gly Phe Ala Arg Ile
                245                 250                 255

Ile Gly Pro Asp Gly Arg Asp Leu Ala Thr Pro Leu Ala Glu Asp Glu
            260                 265                 270

Glu Gly Ile Leu Tyr Ala Asp Ile Asp Leu Ser Ala Ile Thr Leu Ala
        275                 280                 285

Lys Gln Ala Ala Asp Pro Val Gly His Tyr Ser Arg Pro Asp Val Leu
    290                 295                 300

Ser Leu Asn Phe Asn Gln Arg His Thr Thr Pro Val Asn Thr Ala Ile
305                 310                 315                 320
```

Ser Thr Ile His Ala Thr His Thr Leu Val Pro Gln Ser Gly Ala Leu
                325                 330                 335

Asp Gly Val Arg Glu Leu Asn Gly Ala Asp Glu Gln Arg Ala Leu Pro
            340                 345                 350

Ser Thr His Ser Asp Glu Thr Asp Arg Ala Thr Ala Ser Ile
            355                 360                 365

<210> SEQ ID NO 14
<211> LENGTH: 380
<212> TYPE: PRT
<213> ORGANISM: Rhodococcus rhodochrous

<400> SEQUENCE: 14

Met Val Glu Tyr Thr Asn Thr Phe Lys Val Ala Ala Val Gln Ala Gln
1               5                   10                  15

Pro Val Trp Phe Asp Ala Ala Lys Thr Val Asp Lys Thr Val Ser Ile
            20                  25                  30

Ile Ala Glu Ala Ala Arg Asn Gly Cys Glu Leu Val Ala Phe Pro Glu
            35                  40                  45

Val Phe Ile Pro Gly Tyr Pro Tyr His Ile Trp Val Asp Ser Pro Leu
    50                  55                  60

Ala Gly Met Ala Lys Phe Ala Val Arg Tyr His Glu Asn Ser Leu Thr
65                  70                  75                  80

Met Asp Ser Pro His Val Gln Arg Leu Leu Asp Ala Ala Arg Asp His
                85                  90                  95

Asn Ile Ala Val Val Gly Ile Ser Glu Arg Asp Gly Gly Ser Leu
            100                 105                 110

Tyr Met Thr Gln Leu Ile Ile Asp Ala Asp Gly Gln Leu Val Ala Arg
            115                 120                 125

Arg Arg Lys Leu Lys Pro Thr His Val Glu Arg Ser Val Tyr Gly Glu
        130                 135                 140

Gly Asn Gly Ser Asp Ile Ser Val Tyr Asp Met Pro Phe Ala Arg Leu
145                 150                 155                 160

Gly Ala Leu Asn Cys Trp Glu His Phe Gln Thr Leu Thr Lys Tyr Ala
                165                 170                 175

Met Tyr Ser Met His Glu Gln Val His Val Ala Ser Trp Pro Gly Met
            180                 185                 190

Ser Leu Tyr Gln Pro Glu Val Pro Ala Phe Gly Val Asp Ala Gln Leu
        195                 200                 205

Thr Ala Thr Arg Met Tyr Ala Leu Glu Gly Gln Thr Phe Val Val Cys
    210                 215                 220

Thr Thr Gln Val Val Thr Pro Glu Ala His Glu Phe Phe Cys Glu Asn
225                 230                 235                 240

Glu Glu Gln Arg Lys Leu Ile Gly Arg Gly Gly Phe Ala Arg Ile
                245                 250                 255

Ile Gly Pro Asp Gly Arg Asp Leu Ala Thr Pro Leu Ala Glu Asp Glu
            260                 265                 270

Glu Gly Ile Leu Tyr Ala Asp Ile Asp Leu Ser Ala Ile Thr Leu Ala
        275                 280                 285

Lys Gln Ala Ala Asp Pro Val Gly His Tyr Ser Arg Pro Asp Val Leu
    290                 295                 300

Ser Leu Asn Phe Asn Gln Arg Arg Thr Thr Pro Val Asn Thr Pro Leu
305                 310                 315                 320

Ser Thr Ile His Ala Thr His Thr Phe Val Pro Gln Ser Gly Ala Leu
                325                 330                 335

```
Asp Gly Val Arg Glu Leu Asn Gly Ala Asp Glu Gln Arg Ala Leu Pro
            340                 345                 350

Ser Thr His Ser Asp Glu Thr Asp Arg Ala Thr Ala Pro Ser Asp Ser
            355                 360                 365

Gly Ala Pro Val Ala Pro Pro Lys Arg His Gly Val
        370                 375                 380

<210> SEQ ID NO 15
<211> LENGTH: 344
<212> TYPE: PRT
<213> ORGANISM: Gordona terrae

<400> SEQUENCE: 15

Met Thr Thr Asp Tyr Ser Gly Thr Phe Lys Ala Val Thr Gln Ala
  1               5                  10                  15

Glu Pro Val Trp Phe Asp Leu Ser Ala Thr Val Asp Lys Thr Ile Ala
             20                  25                  30

Leu Val Glu Glu Ala Ser Arg Ala Gly Ala Asp Leu Ile Ala Phe Pro
         35                  40                  45

Glu Thr Trp Ile Pro Gly Tyr Pro Trp Phe Leu Trp Leu Asp Ser Val
     50                  55                  60

Ala Trp Gln Ser Gln Tyr Phe Ile Arg Tyr Pro Gln Asn Ser Leu Asp
 65                  70                  75                  80

Leu Asp Gly Ser Glu Phe Ala Ala Ile Arg Glu Ala Ala Arg Lys Asn
                 85                  90                  95

Asp Ile Ala Ile Thr Met Gly Phe Ser Glu Arg Gly His Gly Ser Leu
            100                 105                 110

Tyr Met Gly Gln Ala Val Ile Glu Arg Asp Gly Val Val Val Arg Thr
        115                 120                 125

Arg Arg Lys Leu Lys Pro Thr His Val Glu Arg Thr Leu Phe Gly Glu
    130                 135                 140

Gly Asp Gly Ser Asp Leu Val Val Asp Gln Thr Ser Leu Gly Arg Val
145                 150                 155                 160

Gly Ser Leu Cys Cys Trp Glu His Leu Gln Pro Leu Thr Lys Tyr Ala
                165                 170                 175

Met Tyr Ser Gln His Glu Gln Ile His Ile Ala Ala Trp Pro Ser Phe
            180                 185                 190

Ser Ile Phe Pro Gly Ala Val Tyr Ala Leu Gly Pro Glu Val Asn Thr
        195                 200                 205

Ala Ala Ser Gln Gln Tyr Ala Val Glu Gly Gln Thr Tyr Val Leu Ala
    210                 215                 220

Pro Cys Ala Val Ile Gly Asp Ala Gly Trp Glu Ala Phe Ala Asp Thr
225                 230                 235                 240

Glu Glu Lys Arg Gln Leu Ile His Lys Gly Gly Gly Tyr Ala Arg Ile
                245                 250                 255

Tyr Gly Pro Asp Gly Arg Ser Leu Ala Glu Pro Leu Ala Pro Asn Asp
            260                 265                 270

Glu Gly Ile Leu Tyr Ala Asp Ile Asp Leu Ser Ala Ile Leu Ala Ala
        275                 280                 285

Lys Asn Pro Ala Asp Pro Val Gly His Tyr Ser Arg Pro Asp Val Leu
    290                 295                 300

Arg Leu Gly Phe Asn Lys Ala Pro Gln Pro Lys Val Asn Ile Leu Gly
305                 310                 315                 320

Thr Glu Pro Ser Arg Thr Thr Ser Thr Gln Cys Arg Pro Thr Thr Ile
```

Arg Arg Ser Trp Arg Phe Pro Glu
            340

<210> SEQ ID NO 16
<211> LENGTH: 383
<212> TYPE: PRT
<213> ORGANISM: Rhodococcus rhodochrous

<400> SEQUENCE: 16

Met Ser Ser Asn Pro Glu Leu Lys Tyr Thr Gly Lys Val Lys Val Ala
  1               5                  10                  15

Thr Val Gln Ala Glu Pro Val Ile Leu Asp Ala Asp Ala Thr Ile Asp
                 20                  25                  30

Lys Ala Ile Gly Phe Ile Glu Ala Ala Lys Asn Gly Ala Glu Phe
             35                  40                  45

Leu Ala Phe Pro Glu Val Trp Ile Pro Gly Tyr Pro Tyr Trp Ala Trp
         50                  55                  60

Ile Gly Asp Val Lys Trp Ala Val Ser Asp Phe Ile Pro Lys Tyr His
 65                  70                  75                  80

Glu Asn Ser Leu Thr Leu Gly Asp Asp Arg Met Arg Arg Leu Gln Leu
                 85                  90                  95

Ala Ala Arg Gln Asn Asn Ile Ala Leu Val Met Gly Tyr Ser Glu Lys
            100                 105                 110

Asp Gly Ala Ser Arg Tyr Leu Ser Gln Val Phe Ile Asp Gln Asn Gly
        115                 120                 125

Asp Ile Val Ala Asn Arg Arg Lys Leu Lys Pro Thr His Val Glu Arg
    130                 135                 140

Thr Ile Tyr Gly Glu Gly Asn Gly Thr Asp Phe Leu Thr His Asp Phe
145                 150                 155                 160

Gly Phe Gly Arg Val Gly Gly Leu Asn Cys Trp Glu His Phe Gln Pro
                165                 170                 175

Leu Ser Lys Tyr Met Met Tyr Ser Leu Asn Glu Gln Ile His Val Ala
            180                 185                 190

Ser Trp Pro Ala Met Phe Ala Leu Thr Pro Asp Val His Gln Leu Ser
        195                 200                 205

Val Glu Ala Asn Asp Thr Val Thr Arg Ser Tyr Ala Ile Glu Gly Gln
    210                 215                 220

Thr Phe Val Leu Ala Ser Thr His Val Ile Gly Lys Ala Thr Gln Asp
225                 230                 235                 240

Leu Phe Ala Gly Asp Asp Ala Lys Arg Ala Leu Leu Pro Leu Gly
                245                 250                 255

Gln Gly Trp Ala Arg Ile Tyr Gly Pro Asp Gly Lys Ser Leu Ala Glu
            260                 265                 270

Pro Leu Pro Glu Asp Ala Glu Gly Leu Leu Tyr Ala Glu Leu Asp Leu
        275                 280                 285

Glu Gln Ile Ile Leu Ala Lys Ala Ala Ala Asp Pro Ala Gly His Tyr
    290                 295                 300

Ser Arg Pro Asp Val Leu Ser Leu Lys Ile Asp Thr Arg Asn His Thr
305                 310                 315                 320

Pro Val Gln Tyr Ile Thr Ala Asp Gly Arg Thr Ser Leu Asn Ser Asn
                325                 330                 335

Ser Arg Val Glu Asn Tyr Arg Leu His Gln Leu Ala Asp Ile Glu Lys
            340                 345                 350

Tyr Glu Asn Ala Glu Ala Ala Thr Leu Pro Leu Asp Ala Pro Ala Pro
            355                 360                 365

Ala Pro Ala Pro Glu Gln Lys Ser Gly Arg Ala Lys Ala Glu Ala
370                 375                 380

<210> SEQ ID NO 17
<211> LENGTH: 349
<212> TYPE: PRT
<213> ORGANISM: Klebsiella ozaenae

<400> SEQUENCE: 17

Met Asp Thr Thr Phe Lys Ala Ala Val Gln Ala Glu Pro Val Trp
 1               5                  10                  15

Met Asp Ala Ala Thr Ala Asp Lys Thr Val Thr Leu Val Ala Lys
                20                  25                  30

Ala Ala Ala Ala Gly Ala Gln Leu Val Ala Phe Pro Glu Leu Trp Ile
            35                  40                  45

Pro Gly Tyr Pro Gly Phe Met Leu Thr His Asn Gln Thr Glu Thr Leu
    50                  55                  60

Pro Phe Ile Ile Lys Tyr Arg Lys Gln Ala Ile Ala Ala Asp Gly Pro
65                  70                  75                  80

Glu Ile Glu Lys Ile Arg Cys Ala Ala Gln Glu His Asn Ile Ala Leu
                85                  90                  95

Ser Phe Gly Tyr Ser Glu Arg Ala Gly Arg Thr Leu Tyr Met Ser Gln
            100                 105                 110

Met Leu Ile Asp Ala Asp Gly Ile Thr Lys Ile Arg Arg Arg Lys Leu
            115                 120                 125

Lys Pro Thr Arg Phe Glu Arg Glu Leu Phe Gly Glu Gly Asp Gly Ser
130                 135                 140

Asp Leu Gln Val Ala Gln Thr Ser Val Gly Arg Val Gly Ala Leu Asn
145                 150                 155                 160

Cys Ala Glu Asn Leu Gln Ser Leu Asn Lys Phe Ala Leu Ala Ala Glu
                165                 170                 175

Gly Glu Gln Ile His Ile Ser Ala Trp Pro Phe Thr Leu Gly Ser Pro
            180                 185                 190

Val Leu Val Gly Asp Ser Ile Gly Ala Ile Asn Gln Val Tyr Ala Ala
            195                 200                 205

Glu Thr Gly Thr Phe Val Leu Met Ser Thr Gln Val Val Gly Pro Thr
210                 215                 220

Gly Ile Ala Ala Phe Glu Ile Glu Asp Arg Tyr Asn Pro Asn Gln Tyr
225                 230                 235                 240

Leu Gly Gly Gly Tyr Ala Arg Ile Tyr Gly Pro Asp Met Gln Leu Lys
                245                 250                 255

Ser Lys Ser Leu Ser Pro Thr Glu Glu Gly Ile Val Tyr Ala Glu Ile
            260                 265                 270

Asp Leu Ser Met Leu Glu Ala Ala Lys Tyr Ser Leu Asp Pro Thr Gly
            275                 280                 285

His Tyr Ser Arg Pro Asp Val Phe Ser Val Ser Ile Asn Arg Gln Arg
    290                 295                 300

Gln Pro Ala Val Ser Glu Val Ile Asp Ser Asn Gly Asp Glu Asp Pro
305                 310                 315                 320

Arg Ala Ala Cys Glu Pro Asp Glu Gly Asp Arg Glu Val Val Ile Ser
                325                 330                 335

Thr Ala Ile Gly Val Leu Pro Arg Tyr Cys Gly His Ser
            340                 345

<210> SEQ ID NO 18
<211> LENGTH: 354
<212> TYPE: PRT
<213> ORGANISM: Comamonas testosteroni

<400> SEQUENCE: 18

Met Lys Asn Tyr Pro Thr Val Lys Val Ala Ala Val Gln Ala Ala Pro
1               5                   10                  15

Val Phe Met Asn Leu Glu Ala Thr Val Asp Lys Thr Cys Lys Leu Ile
            20                  25                  30

Ala Glu Ala Ala Ser Met Gly Ala Lys Val Ile Gly Phe Pro Glu Ala
        35                  40                  45

Phe Ile Pro Gly Tyr Pro Tyr Trp Ile Trp Thr Ser Asn Met Asp Phe
    50                  55                  60

Thr Gly Met Met Trp Ala Val Leu Phe Lys Asn Ala Ile Glu Ile Pro
65                  70                  75                  80

Ser Lys Glu Val Gln Gln Ile Ser Asp Ala Ala Lys Lys Asn Gly Val
                85                  90                  95

Tyr Val Cys Val Ser Val Ser Glu Lys Asp Asn Ala Ser Leu Tyr Leu
            100                 105                 110

Thr Gln Leu Trp Phe Asp Pro Asn Gly Asn Leu Ile Gly Lys His Arg
        115                 120                 125

Lys Phe Lys Pro Thr Ser Ser Glu Arg Ala Val Trp Gly Asp Gly Asp
    130                 135                 140

Gly Ser Met Ala Pro Val Phe Lys Thr Glu Tyr Gly Asn Leu Gly Gly
145                 150                 155                 160

Leu Gln Cys Trp Glu His Ala Leu Pro Leu Asn Ile Ala Ala Met Gly
                165                 170                 175

Ser Leu Asn Glu Gln Val His Val Ala Ser Trp Pro Ala Phe Val Pro
            180                 185                 190

Lys Gly Ala Val Ser Ser Arg Val Ser Ser Val Cys Ala Ser Thr
    195                 200                 205

Asn Ala Met His Gln Ile Ile Ser Gln Phe Tyr Ala Ile Ser Asn Gln
210                 215                 220

Val Tyr Val Ile Met Ser Thr Asn Leu Val Gly Gln Asp Met Ile Asp
225                 230                 235                 240

Met Ile Gly Lys Asp Glu Phe Ser Lys Asn Phe Leu Pro Leu Gly Ser
                245                 250                 255

Gly Asn Thr Ala Ile Ile Ser Asn Thr Gly Glu Ile Leu Ala Ser Ile
            260                 265                 270

Pro Gln Asp Ala Glu Gly Ile Ala Val Ala Glu Ile Asp Leu Asn Gln
    275                 280                 285

Ile Ile Tyr Gly Lys Trp Leu Leu Asp Pro Ala Gly His Tyr Ser Thr
290                 295                 300

Pro Gly Phe Leu Ser Leu Thr Phe Asp Gln Ser Glu His Val Pro Val
305                 310                 315                 320

Lys Lys Ile Gly Glu Gln Thr Asn His Phe Ile Ser Tyr Glu Asp Leu
                325                 330                 335

His Glu Asp Lys Met Asp Met Leu Thr Ile Pro Pro Arg Arg Val Ala
            340                 345                 350

Thr Ala

<210> SEQ ID NO 19

```
<211> LENGTH: 356
<212> TYPE: PRT
<213> ORGANISM: Alcaligenes faecalis

<400> SEQUENCE: 19

Met Gln Thr Arg Lys Ile Val Arg Ala Ala Val Gln Ala Ala Ser
1               5                   10                  15

Pro Asn Tyr Asp Leu Ala Thr Gly Val Asp Lys Thr Ile Glu Leu Ala
            20                  25                  30

Arg Gln Ala Arg Asp Glu Gly Cys Asp Leu Ile Val Phe Gly Glu Thr
        35                  40                  45

Trp Leu Pro Gly Tyr Pro Phe His Val Trp Leu Gly Ala Pro Ala Trp
    50                  55                  60

Ser Leu Lys Tyr Ser Ala Arg Tyr Tyr Ala Asn Ser Leu Ser Leu Asp
65                  70                  75                  80

Ser Ala Glu Phe Gln Arg Ile Ala Gln Ala Ala Arg Thr Leu Gly Ile
                85                  90                  95

Phe Ile Ala Leu Gly Tyr Ser Glu Arg Ser Gly Gly Ser Leu Tyr Leu
            100                 105                 110

Gly Gln Cys Leu Ile Asp Asp Lys Gly Gln Met Leu Trp Ser Arg Arg
        115                 120                 125

Lys Leu Lys Pro Thr His Val Glu Arg Thr Val Phe Gly Glu Gly Tyr
130                 135                 140

Ala Arg Asp Leu Ile Val Ser Asp Thr Glu Leu Gly Arg Val Gly Ala
145                 150                 155                 160

Leu Cys Cys Trp Glu His Leu Ser Pro Leu Ser Lys Tyr Ala Leu Tyr
                165                 170                 175

Ser Gln His Glu Ala Ile His Ile Ala Ala Trp Pro Ser Phe Ser Leu
            180                 185                 190

Tyr Ser Glu Gln Ala His Ala Leu Ser Ala Lys Val Asn Met Ala Ala
        195                 200                 205

Ser Gln Ile Tyr Ser Val Glu Gly Gln Cys Phe Thr Ile Ala Ala Ser
210                 215                 220

Ser Val Val Thr Gln Glu Thr Leu Asp Met Leu Glu Val Gly Glu His
225                 230                 235                 240

Asn Ala Ser Leu Leu Lys Val Gly Gly Gly Ser Ser Met Ile Phe Ala
                245                 250                 255

Pro Asp Gly Arg Thr Leu Ala Pro Tyr Leu Pro His Asp Ala Glu Gly
            260                 265                 270

Leu Ile Ile Ala Asp Leu Asn Met Glu Glu Ile Ala Phe Ala Lys Ala
        275                 280                 285

Ile Asn Asp Pro Val Gly His Tyr Ser Lys Pro Glu Ala Thr Arg Leu
290                 295                 300

Val Leu Asp Leu Gly His Arg Glu Pro Met Thr Arg Val His Ser Lys
305                 310                 315                 320

Ser Val Ile Gln Glu Glu Ala Pro Gly Pro His Val Gln Ser Thr Ala
                325                 330                 335

Ala Pro Val Ala Val Ser Gln Thr Gln Asp Ser Asp Thr Leu Leu Val
            340                 345                 350

Gln Glu Pro Ser
        355

<210> SEQ ID NO 20
<211> LENGTH: 367
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 20

```
Met Ala Val Pro Pro Ser Thr Asn Glu Met Thr Phe Ala Glu Val Met
  1               5                  10                  15

Asn Gly Ser Ser Thr Pro Thr Val Arg Ala Val Gln Ala Ser Thr Val
             20                  25                  30

Phe Tyr Asp Thr Pro Ala Thr Leu Asp Lys Ala Glu Leu Ile Ala Glu
         35                  40                  45

Ala Ala Ser Asn Gly Ala Leu Val Val Phe Pro Glu Ala Phe Ile Gly
     50                  55                  60

Tyr Pro Arg Gly Ser Thr Phe Gly Tyr His Leu Trp Gly Pro Ala Gly
 65                  70                  75                  80

Arg Asp Glu Phe Arg Lys Tyr His Ala Ala Ile Asp Val Pro Gly Pro
                 85                  90                  95

Glu Val Arg Leu Ala Asp Ala Ala Arg Lys Asn Asn Val Tyr Leu Val
            100                 105                 110

Met Gly Val Glu Arg Asp Gly Tyr Thr Leu Tyr Cys Thr Gln Leu Phe
        115                 120                 125

Phe Asp Pro Gln Gly Gln Phe Leu Gly Lys His Arg Lys Leu Pro Thr
130                 135                 140

His Leu Glu Arg Cys Ile Trp Gly Gly Asp Gly Ser Thr Ile Pro
145                 150                 155                 160

Val Tyr Asp Thr Pro Leu Gly Lys Gly Ala Leu Ile Cys Trp Glu Asn
                165                 170                 175

Arg Met Pro Leu Leu Arg Thr Ala Met Tyr Ala Lys Gly Glu Ile Cys
            180                 185                 190

Ala Ser Trp Pro Thr Ala Asp Ser Arg Trp Gln Ser Ser Met Thr Pro
        195                 200                 205

Glu Val Pro Ala Leu Gly Val Asp Ala Asn Leu Ala Gln His Ala Leu
    210                 215                 220

Glu Gly Gly Cys Phe Val Leu Ser Ala Thr Gln Phe Cys Arg Lys Asp
225                 230                 235                 240

Tyr Pro Pro Pro Pro Glu Tyr Leu Phe Gly Asp Asp Glu Lys Arg Pro
                245                 250                 255

Asp Ser Ile Val Gly Gly Gly Ser Val Ile Ile Ser Pro Asp Gly
            260                 265                 270

Arg Val Leu Ala Gly Pro Leu Asn Tyr Gly Glu Gly Leu Ile Ala Asp
        275                 280                 285

Leu Asp Leu Gly Ile Ala Arg Ala Lys Phe Asp Phe Asp Pro Val Gly
    290                 295                 300

His Tyr Ser Arg Pro Asp Val Leu Ser Leu Thr Val Asn Glu His Pro
305                 310                 315                 320

Lys Pro Val Ser Phe Val Thr Ser Glu Lys Ala Glu Ser Thr Ser Pro
                325                 330                 335

Gly Ala Leu Gly Val Arg Gly Ala Asp Glu Gln Arg Ala Leu Pro Ser
            340                 345                 350

His Ser Asp Glu Thr Asp Arg Ala Thr Ala Pro Asp Ala Pro Pro
        355                 360                 365
```